(12) United States Patent
Gross et al.

(10) Patent No.: US 8,403,953 B2
(45) Date of Patent: Mar. 26, 2013

(54) BALLOON WITH RIGID TUBE FOR OCCLUDING THE UTERINE ARTERY

(75) Inventors: Yossi Gross, Moshav Mazor (IL); Eliahu Eliachar, Haifa (IL); Dan Sade Hochstadter, Kibbutz Bet Alfa (IL); Jacob Cohen, Ramat HaSharon (IL); Hernam Weiss, Beit Shemesh (IL); Nir Lilach, K'far Yehoshua (IL)

(73) Assignee: Fibro Control, Inc., Wilmington, DE (US)

( * ) Notice: Subject to any disclaimer, the term of this patent is extended or adjusted under 35 U.S.C. 154(b) by 826 days.

(21) Appl. No.: 12/509,732

(22) Filed: Jul. 27, 2009

(65) Prior Publication Data
US 2011/0022073 A1    Jan. 27, 2011

(51) Int. Cl.
*A61M 29/00* (2006.01)
(52) U.S. Cl. .................................................. 606/193
(58) Field of Classification Search .............. 606/119, 606/193, 191
See application file for complete search history.

(56) References Cited

U.S. PATENT DOCUMENTS

| | | |
|---|---|---|
| 3,730,186 A | 5/1973 | Edmunds, Jr. et al. |
| 4,344,438 A | 8/1982 | Schultz |
| 4,430,076 A | 2/1984 | Harris |
| 4,881,939 A | 11/1989 | Newman |
| 5,001,054 A | 3/1991 | Wagner |
| 5,246,867 A | 9/1993 | Lakowicz et al. |
| 5,338,297 A | 8/1994 | Kocur et al. |
| 5,626,134 A | 5/1997 | Zuckerman |
| 5,688,234 A | 11/1997 | Frisbie |
| 5,766,151 A | 6/1998 | Valley et al. |
| 5,770,454 A | 6/1998 | Essenpreis et al. |
| 5,976,069 A * | 11/1999 | Navia et al. ..................... 600/37 |
| 5,979,453 A | 11/1999 | Savage et al. |
| 5,998,204 A | 12/1999 | Tsien et al. |
| 6,004,260 A | 12/1999 | Thompson |
| 6,059,766 A | 5/2000 | Greff |

(Continued)

FOREIGN PATENT DOCUMENTS

| | | |
|---|---|---|
| GB | 2 302 025 A | 1/1997 |
| JP | 5-177001 A | 7/1993 |

(Continued)

OTHER PUBLICATIONS

An Office Action dated Jul. 20, 2011 which issued during the prosecution of U.S. Appl. No. 11/591,044.

(Continued)

*Primary Examiner* — Gary Jackson
*Assistant Examiner* — Lindsey Bachman
(74) *Attorney, Agent, or Firm* — Sughrue Mion, PLLC

(57) ABSTRACT

Apparatus is provided for use with a subject's body, vagina, vaginal fornix, uterus, and uterine artery. A fornix-engaging structure is inserted into the vagina and engages the vaginal fornix. A rod is inserted into the subject's body via the fornix-engaging structure, such that a distal end of the rod passes through vaginal tissue at a first vaginal site until the distal end of the rod is at a first extrauterine site outside of the uterine artery, but in a vicinity of a portion of the uterine artery that supplies a uterine fibroid. A rod-guide is coupled to the fornix-engaging structure, and guides the distal end of the rod to the first extrauterine site. A uterine artery compression device is disposed on the distal end of the rod. Other embodiments are also described.

13 Claims, 15 Drawing Sheets

U.S. PATENT DOCUMENTS

| | | | |
|---|---|---|---|
| 6,163,714 | A | 12/2000 | Stanley et al. |
| 6,183,502 | B1 | 2/2001 | Takeuchi |
| 6,197,534 | B1 | 3/2001 | Lakowicz et al. |
| 6,217,529 | B1 | 4/2001 | Wax et al. |
| 6,254,601 | B1 | 7/2001 | Burbank et al. |
| 6,264,676 | B1 | 7/2001 | Gellman et al. |
| 6,382,214 | B1 | 5/2002 | Raz et al. |
| 6,425,867 | B1 | 7/2002 | Vaezy |
| 6,521,446 | B2 | 2/2003 | Hellinga |
| 6,540,693 | B2 | 4/2003 | Burbank et al. |
| 6,550,482 | B1 | 4/2003 | Burbank et al. |
| 6,602,251 | B2 | 8/2003 | Burbank et al. |
| 6,625,479 | B1 | 9/2003 | Weber et al. |
| 6,635,065 | B2 | 10/2003 | Burbank et al. |
| 6,638,286 | B1 | 10/2003 | Burbank et al. |
| 6,679,851 | B2 | 1/2004 | Burbank et al. |
| RE38,525 | E | 6/2004 | Stanley et al. |
| 6,764,488 | B1 | 7/2004 | Burbank et al. |
| 6,905,506 | B2 | 6/2005 | Burbank et al. |
| 6,958,044 | B2 | 10/2005 | Burbank et al. |
| 7,141,057 | B2 | 11/2006 | Burbank et al. |
| 7,172,603 | B2 * | 2/2007 | Burbank et al. ............... 606/119 |
| 7,207,996 | B2 | 4/2007 | Burbank et al. |
| 7,223,279 | B2 | 5/2007 | Burbank et al. |
| 7,229,465 | B2 | 6/2007 | Burbank et al. |
| 7,264,596 | B2 | 9/2007 | Burbank et al. |
| 7,329,265 | B2 | 2/2008 | Burbank et al. |
| 7,333,844 | B2 | 2/2008 | Jones et al. |
| 7,594,890 | B2 | 9/2009 | Burbank et al. |
| 2002/0165579 | A1 | 11/2002 | Burbank et al. |
| 2002/0188306 | A1 | 12/2002 | Burbank et al. |
| 2003/0120286 | A1 | 6/2003 | Burbank et al. |
| 2003/0120306 | A1 | 6/2003 | Burbank et al. |
| 2003/0216759 | A1 | 11/2003 | Burbank et al. |
| 2004/0097788 | A1 | 5/2004 | Mourlas et al. |
| 2004/0097961 | A1 | 5/2004 | Burbank et al. |
| 2004/0098035 | A1 | 5/2004 | Wada |
| 2004/0117652 | A1 | 6/2004 | Burbank et al. |
| 2005/0101974 | A1 | 5/2005 | Burbank et al. |
| 2005/0113852 | A1 | 5/2005 | Burbank et al. |
| 2005/0143674 | A1 | 6/2005 | Burbank et al. |
| 2005/0187561 | A1 | 8/2005 | Lee-Sepsick et al. |
| 2005/0197594 | A1 | 9/2005 | Burbank et al. |
| 2005/0228416 | A1 | 10/2005 | Burbank et al. |
| 2005/0245842 | A1 | 11/2005 | Burbank et al. |
| 2006/0000479 | A9 * | 1/2006 | Burbank et al. ............... 128/898 |
| 2006/0094983 | A1 | 5/2006 | Burbank et al. |
| 2006/0106109 | A1 | 5/2006 | Burbank et al. |
| 2006/0241337 | A1 | 10/2006 | Jones et al. |
| 2007/0049973 | A1 | 3/2007 | Burbank et al. |
| 2007/0173863 | A1 | 7/2007 | Burbank et al. |
| 2007/0203505 | A1 | 8/2007 | Burbank et al. |
| 2007/0265613 | A1 | 11/2007 | Edelstein et al. |
| 2008/0039888 | A1 | 2/2008 | Doare et al. |
| 2008/0188863 | A1 * | 8/2008 | Chu ............................. 606/119 |
| 2008/0200924 | A1 | 8/2008 | Burbank et al. |
| 2009/0043295 | A1 | 2/2009 | Arnal et al. |
| 2009/0054916 | A1 * | 2/2009 | Meier et al. ................... 606/158 |
| 2009/0093758 | A1 | 4/2009 | Gross |
| 2009/0287088 | A1 | 11/2009 | Burbank et al. |

FOREIGN PATENT DOCUMENTS

| | | |
|---|---|---|
| JP | 10-229986 A | 9/1998 |
| WO | WO 97/17105 | 5/1997 |
| WO | 00/33724 A2 | 6/2000 |
| WO | WO 01/80713 | 11/2001 |
| WO | 02/051320 A2 | 7/2002 |
| WO | WO 02/078521 | 10/2002 |
| WO | WO 02/078522 | 10/2002 |
| WO | WO 02/078549 | 10/2002 |
| WO | WO 02/100286 | 12/2002 |
| WO | WO 03/007827 | 1/2003 |
| WO | WO 2004/045420 | 6/2004 |
| WO | WO 2004/045422 | 6/2004 |
| WO | WO 2004/045426 | 6/2004 |
| WO | WO 2004/045430 | 6/2004 |
| WO | WO 2004/069025 | 8/2004 |
| WO | WO 2006/086234 | 8/2006 |
| WO | WO 2007/027392 | 3/2007 |
| WO | WO 2008/012802 | 1/2008 |

OTHER PUBLICATIONS

An Office Action dated Jan. 5, 2011, which issued during the prosecution of Applicant's U.S. Appl. No. 11/591,044.

An International Search Report and a Written Opinion, both dated Jan. 20, 2011, which issued during the prosecution of Applicant's PCT/IL10/00610.

"Abdominal hysterectomy: a new approach for young gynaecologists," by Dutta, J Indian Med Assoc. Oct. 1997;95(10):556-8. (an abstract).

"A model for studying chronic reduction in uterine blood flow in pregnant sheep," by Clark et al., Am J Physiol Heart Circ Physiol 242: H297-H301, 1982.

"A modified technique for hemostasis during myomectomy," by DeLancey, Surgery Gynecology and Obstetrics, 1992, vol. 174, Pt 2, pp. 153-154.

"An in vivo study of the effects of ischaemia on uterine contraction, intracellular pH and metabolites in the rat," by Harrison et al., Journal of Physiology (1994), 476.2, pp. 349-354.

"Cervical ectopic pregnancy," by Rahimi et al., J Am Assoc Gynecol Laparosc. Aug. 1996;3(4, Supplement):S41 (an abstract).

"Cervical pregnancy: three case reports and a review of the literature," by Van de Meerssche et al., Hum Reprod. Jul. 1995;10(7):1850-5 (an abstract).

"Uterine artery ligation in the control of postcesarean hemorrhage," by O'Leary, J Reprod Med. Mar. 1995;40(3):189-93 (an abstract).

"Common hepatic artery pseudoaneurysm secondary to pancreatitis," by Fava et al., Surg Endosc (1994) 8:1223-1226.

"Devascularization of craniofacial tumors by percutaneous tumor puncture," by Cacasco et al., AJNR Am J Neuroradiol 15:1233-1239, Aug. 1994.

"Embolization of uterine leiomyomata: current concepts in management," Braude et al., Human Reproduction Update 2000, vol. 6, No. 6, pp. 603-608.

"Experience with internal iliac artery ligation in obstetrics and gynaecological practice," by Jain, J Indian Med Assoc. Sep. 1990;88(9):246-7 (an abstract).

"Extraperitoneal Laparoscopic Hysterectomy for Fibroid Uteri," by Kadar, J Am Assoc Gynecol Laparosc. Aug. 1996;3(4, Supplement):S20 (an abstract).

"Indications for Hysterectomy: Have They Changed," by Steege, Clinical Obstetrics and Gynecology:vol. 40(4)Dec. 1997pp. 878-885.

"Laparoscopic Uterine Artery Ligation for Treatment of Symptomatic Adenomyosis," by Wang et al., Presented at the 10th annual congress of the International Society for Gynecologic Endoscopy, Chicago, Illinois, Mar. 28-31, 2001 (an abstract).

The Journal of the American Association of Gynecologic Laparoscopists vol. 9, Issue 2, May 2002, pp. 191-198, by Lichtinger, Presented at the 30th annual meeting of the American Association of Gynecologic Laparoscopists, San Francisco, California, Nov. 16-19, 2001. (an abstract).

"Ligation of uterine arteries, per vaginum, in a case of recurrent secondary post partum haemorrhage following caesarean section," by Ross, Aust. N.Z.J. Obstet. Gynaec. (1965) 5:215.

"Own experience with internal iliac and ovarian artery ligation in gynecological and oncological surgeries," by Neuberg, Ginekol Pol. May 1998;69(5):358-62 (an abstract).

"Pelvic anatomy of the ureter in relation to surgery performed through the vagina," by Hofmeister, Clinical Obstetrics and Gynecology, vol. 25, No. 4, Dec. 1982.

"Preliminary experience with uterine artery ligation for symptomatic uterine leiomyomas," by Lee et al., Journal of the American Association of Gynecologic Laparoscopists, Aug. 1999, vol. 6, No. 3.

"The management of uterine leiomyomas," by Lefebvre et al., SOGC Clinical Practice Guidelines, No. 128, May 2003.

"Therapeutic embolization with detachable silicone balloons. Early clinical experience," by White et al., JAMA. Mar. 23, 1979;241(12):1257-60 (an abstract).

"Treatment outcomes of uterine artery embolization and laparoscopic uterine artery ligation for uterine myoma," by Park et al., Yonsei Medical Journal vol. 44, No. 4, pp. 694-702, 2003.

"Two uterine arterial management methods in laparoscopic hysterectomy," by Song et al., J Obstet Gynaecol Res. Apr. 1998;24(2):145-51 (an abstract).

"Use of a large Foley catheter balloon to control postpartum hemorrhage resulting from a low placental implantation. A report of two cases," by Bowen et al., J Reprod Med. Aug. 1985;30(8):623-5 (an abstract).

"Uterine artery embolization: An underused method of controlling pelvic hemorrhage," by Vedantham et al., American Journal of Obstetrics & Gynecology Apr. 1997, 176:4.

"Vaginal uterine artery ligation avoids high blood loss and puerperal hysterectomy in postpartum hemorrhage," by Hebisch et al., Obstetrics & Gynecology vol. 100, No. 3, Sep. 2002.

"Uterine artery occlusion by embolization or surgery for the treatment of fibroids: a unifying hypothesis—transient uterine ischemia," by Burbank et al., Journal of the American Association of Gynecologic Laparoscopists, Nov. 2007, vol. 7, No. 4.

"Vaginal ligature of uterine arteries during postpartum hemorrhage," by Philippe et al., International Journal of Gynecology and Obstetrics 56 (1997) 267-270.

P. Turkewitsch, "The synthesis of fluorescent chemosensors responsive to cAMP and other nucleotides", Montreal Quebec, Sep. 1998.

G. Gilardi, et al., "Spectroscopic properties of an engineered maltose binding protein", Protein Engineering vol. 10 No. 5, pp. 479-486, 1997.

Homme W. Hellinga, et al., "Protein engineering and the development of generic biosensors", TIBTECH Apr. 1998, vol. 16.

S.P.J. Higson, et al., "Biosensors: a viable monitoring technology?", Med. & Biol. Eng. & Comput., 1994, 32, 601-609.

Leah Tolosa, et al., "Optical assay for glucose based on the luminescnence decay time of the long wavelength dye Cy5™", Sensors and Actuators B 45 (1997) 93-99.

Leah Tolosa, et al., "Glucose sensor for low-cost lifetime-based sensing using a genetically engineered protein", Analytical Biochemistry 267, 114-120 (1999).

K. Yamada, et al., "Measurement of glucose uptake and intracellular calcium concentration in single, living pancreatic β-cells", The Journal of Biological Chemistry, vol. 275, No. 29, Jul. 2000, pp. 22278-22283.

Leah Tolosa, et al., "Lifetime-based sensing of glucose using energy transfer with a long lifetime donor", Analytical Biochemistry 250, 102-108, 1997.

J.C. Pickup, et al., "Fluorescence-based glucose sensors", Biosensors and Bioelectronics 20 (2005) 2555-2565.

M. Sakurada, et al., "Relation between glucose-stimulated insulin secretion and intracellular calcium accumulation studied with a superfusion system of a glucose-responsive pancreatic β-cell line MIN6", Endo. 1993, vol. 132, No. 6.

J.S. Marvin, et al., "The rational design of allosteric interactions in a monomeric protein and its applications to the construction of biosensors", Proc. Natl. Acad. Sci. USA vol. 94, pp. 4366-4371, Apr. 1997.

H.J. Philippe, et al., "Vaginal ligature of uterine arteries during postpartum hemorrhage", International Journal of Gynecology & Obstetrics 56 (1997) 267-270.

An Office Action dated Jan. 20, 2012, which issued during the prosecution of U.S. Appl. No. 11/591,044.

An English translation of an Office Action dated Jun. 8, 2012, which issued during the prosecution of Japanese Patent Application No. 2009-521412.

U.S. Office Action dated Sep. 25, 2012, issued in U.S. Appl. No. 11/591,044.

* cited by examiner

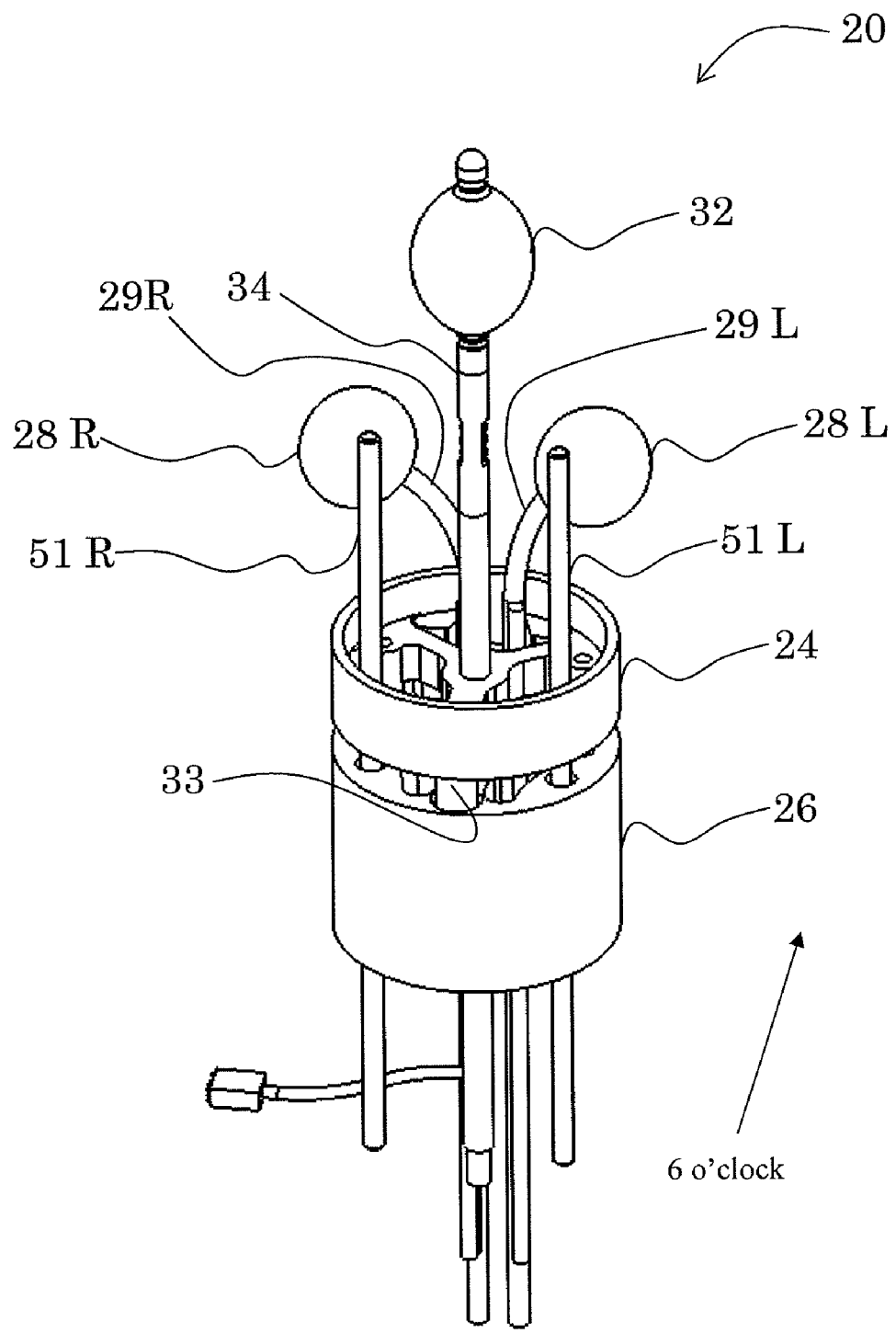

3 o'clock ⟶

3 o'clock ⟶

BALLOON WITH RIGID TUBE FOR OCCLUDING THE UTERINE ARTERY

CROSS-REFERENCES TO RELATED APPLICATIONS

The present patent application is related to U.S. patent application Ser. No. 12/374,884 to Gross, which is the US national phase of PCT Application PCT/IL2007/000911 to Gross, filed Jul. 18, 2007, entitled, "Fibroid treatment apparatus and method," which is a continuation-in-part of U.S. patent application Ser. No. 11/591,044 to Gross, filed Oct. 31, 2006, entitled, "Fibroid treatment apparatus and method," which claims priority from U.S. Provisional Patent Application 60/820,130 to Gross, filed Jul. 24, 2006, entitled, "Fibroid treatment apparatus and method." All of the above-referenced applications are incorporated herein by reference.

FIELD OF THE INVENTION

The present invention generally relates to medical apparatus. Specifically, the present invention relates to apparatus and methods for occluding a subject's uterine artery.

BACKGROUND OF THE INVENTION

Uterine fibroids are benign tumors of muscle and connective tissue that develop within, or are attached to, the uterine wall.

PCT Publication WO 08/012802 to Gross describes apparatus including a tube that is configured to pass into a patient's vagina and to penetrate vaginal tissue until a distal tip of the tube is outside of a uterine artery of the patient, but in a vicinity of a portion of the uterine artery that supplies a uterine fibroid. A balloon, disposed at the distal tip, is inflated to cause local squeezing of the portion of the uterine artery to an extent sufficient to occlude the uterine artery.

Vascular Control Systems (San Juan Capistrano, Calif.), which was acquired by Johnson & Johnson, has developed a device called the Flostat. According to the company, the primary element of the Flostat system is a Doppler guided clamp designed for bilateral temporary occlusion of the uterine arteries. The device is currently indicated for use during conservative gynecologic procedures such as laparoscopic myomectomy.

U.S. Pat. Nos. 6,254,601 and 6,602,251, both to Burbank et al., describe devices and methods for treating a uterine disorder which receives its blood supply from a uterine artery. In particular, uterine fibroids are described as being treated by occluding the uterine arteries using trans-vaginal, trans-uterine, transrectal, or retroperitoneal approaches. The devices and methods are described as being used by a patient's gynecologist in the course of treatment, avoiding the need for referrals to specialist practitioners and for more radical treatments, such as hysterectomies. The methods include both temporary and permanent occlusion of the arteries. A cannula is described as carrying an imaging device and a member which will penetrate tissue, the member including a device which partially or completely, and temporarily or permanently, occludes a uterine artery.

CooperSurgical® (CT, USA) manufactures The Rumi System®, which includes a silicone intrauterine balloon.

The following references may be of interest:
U.S. Pat. No. 7,333,844 to Jones et al.
U.S. Pat. No. 7,329,265 to Burbank et al.
U.S. Pat. No. 7,264,596 to Burbank et al.
U.S. Pat. No. 7,229,465 to Burbank et al.
U.S. Pat. No. 7,223,279 to Burbank et al.
U.S. Pat. No. 7,207,996 to Burbank et al.
U.S. Pat. No. 7,172,603 to Burbank et al.
U.S. Pat. No. 7,141,057 to Burbank et al.
U.S. Pat. No. 6,958,044 to Burbank et al.
U.S. Pat. No. 6,905,506 to Burbank et al.
U.S. Pat. No. 6,764,488 to Burbank et al.
U.S. Pat. No. 6,679,851 to Burbank et al.
U.S. Pat. No. 6,638,286 to Burbank et al.
U.S. Pat. No. 6,635,065 to Burbank et al.
U.S. Pat. No. 6,550,482 to Burbank et al.
U.S. Pat. No. 6,540,693 to Burbank et al.
U.S. Pat. No. 6,425,867 to Vaezy
U.S. Pat. No. 6,059,766 to Greff
U.S. Pat. No. 5,979,453 to Savage
US Patent Application Publication 2009/0093758 to Gross
US Patent Application Publication 2007/0203505 to Burbank et al.
US Patent Application Publication 2007/0173863 to Burbank et al.
US Patent Application Publication 2007/0049973 to Burbank et al.
US Patent Application Publication 2006/0241337 to Jones et al.
US Patent Application Publication 2006/0106109 to Burbank et al.
US Patent Application Publication 2006/0094983 to Burbank et al.
US Patent Application Publication 2006/0000479 to Burbank et al.
US Patent Application Publication 2005/0245842 to Burbank et al.
US Patent Application Publication 2005/0228416 to Burbank et al.
US Patent Application Publication 2005/0197594 to Burbank et al.
US Patent Application Publication 2005/0143674 to Burbank et al.
US Patent Application Publication 2005/0113852 to Burbank et al.
US Patent Application Publication 2005/0101974 to Burbank et al.
US Patent Application Publication 2004/0117652 to Burbank et al.
US Patent Application Publication 2004/0097961 to Burbank et al.
US Patent Application Publication 2004/0097788 to Mourlas et al.
US Patent Application Publication 2003/0216759 to Burbank et al.
US Patent Application Publication 2003/0120306 to Burbank et al.
US Patent Application Publication 2003/0120286 to Burbank et al.
US Patent Application Publication 2002/0188306 to Burbank et al.
US Patent Application Publication 20020165579 to Burbank et al.
PCT Publication WO 07/027,392 to Burbank et al.
PCT Publication WO 06/086,234 to McIntyre et al.
PCT Publication WO 04/069,025 to Burbank et al.
PCT Publication WO 04/045,430 to Burbank et al.
PCT Publication WO 04/045,426 to Burbank et al.
PCT Publication WO 04/045,422 to Burbank et al.
PCT Publication WO 04/045,420 to Burbank et al.
PCT Publication WO 03/007,827 to Burbank et al.
PCT Publication WO 02/100,286 to Burbank et al.

PCT Publication WO 02/078,549 to Burbank et al.
PCT Publication WO 02/078,522 to Burbank et al.
PCT Publication WO 02/078,521 to Burbank et al.
PCT Publication WO 01/080,713 to Burbank et al.
PCT Publication WO 97/017,105 to Savage "Abdominal hysterectomy: a new approach for young gynaecologists," by Dutta, *J Indian Med Assoc.* 1997 October; 95(10):556-8

"A model for studying chronic reduction in uterine blood flow in pregnant sheep," by Clark et al., *Am J Physiol Heart Circ Physiol* 242: H297-H301, 1982

"A modified technique for hemostasis during myomectomy," by DeLancey, *Surgery Gynecology and Obstetrics*, 1992, Vol. 174, Pt 2, pp. 153-154

"An in vivo study of the effects of ischaemia on uterine contraction, intracellular pH and metabolites in the rat," by Harrison et al., *Journal of Physiology* (1994), 476.2, pp. 349-354

"Cervical ectopic pregnancy," by Rahimi et al., *J Am Assoc Gynecol Laparosc.* 1996 August; 3(4, Supplement):S41

"Cervical pregnancy: three case reports and a review of the literature," by Van de Meerssche et al., *Hum Reprod.* 1995 July; 10(7):1850-5

"Cervical pregnancy treated by ligation of the descending branch of the uterine arteries. Case report," by Ratten, *Br J Obstet Gynaecol.* 1983 April; 90(4):367-71

"Common hepatic artery pseudoaneurysm secondary to pancreatitis," by Fava et al., *Surg Endosc* (1994) 8:1223-1226

"Devascularization of craniofacial tumors by percutaneous tumor puncture," by Cacasco et al., *AJNR Am J Neuroradiol* 15:1233-1239, August 1994

"Embolization of uterine leiomyomata: current concepts in management," Braude et al., *Human Reproduction Update* 2000, Vol. 6, No. 6, pp. 603-608

"Experience with internal iliac artery ligation in obstetrics and gynaecological practice," by Jain, *J Indian Med Assoc.* 1990 September; 88(9):246-7

"Extraperitoneal Laparoscopic Hysterectomy for Fibroid Uteri," by Kadar, *J Am Assoc Gynecol Laparosc.* 1996 August; 3(4, Supplement):S20

"Indications for Hysterectomy: Have They Changed," by Steege, *Clinical Obstetrics and Gynecology*: Volume 40(4) December 1997 pp 878-885

"Laparoscopic Uterine Artery Ligation for Treatment of Symptomatic Adenomyosis," by Wang et al., *Presented at the 10th annual congress of the International Society for Gynecologic Endoscopy*, Chicago, Ill., Mar. 28-31, 2001

"Laparoscopic Uterine Artery Occlusion for Symptomatic Leiomyomas," by Lichtinger, *Presented at the 30th annual meeting of the American Association of Gynecologic Laparoscopists*, San Francisco, Calif., Nov. 16-19, 2001

"Ligation of uterine arteries, per vaginum, in a case of recurrent secondary post partum haemorrhage following caesarean section," by Ross, *Aust. N.Z.J. Obstet. Gynaec.* (1965) 5:215

"Own experience with internal iliac and ovarian artery ligation in gynecological and oncological surgeries," by Neuberg, *Ginekol Pol.* 1998 May; 69(5):358-62

"Pelvic anatomy of the ureter in relation to surgery performed through the vagina," by Hofmeister, *Clinical Obstetrics and Gynecology*, Vol. 25, No. 4, December 1982

"Preliminary experience with uterine artery ligation for symptomatic uterine leiomyomas," by Lee et al., *Journal of the American Association of Gynecologic Laparoscopists*, August 1999, Vol. 6, No. 3

"The management of uterine leiomyomas," by Lefebvre et al., *SOGC Clinical Practice Guidelines*, No. 128, May 2003

"Therapeutic embolization with detachable silicone balloons. Early clinical experience," by White et al., *JAMA*. 1979 Mar. 23; 241(12):1257-60

"Treatment outcomes of uterine artery embolization and laparoscopic uterine artery ligation for uterine myoma," by Park et al., Yonsei Medical Journal Vol. 44, No. 4, pp. 694-702, 2003

"Two uterine arterial management methods in laparoscopic hysterectomy," by Song et al., *J Obstet Gynaecol Res.* 1998 April; 24 (2):145-51

"Use of a large Foley catheter balloon to control postpartum hemorrhage resulting from a low placental implantation. A report of two cases," by Bowen et al., *J Reprod Med.* 1985 August; 30(8):623-5

"Uterine artery embolization: An underused method of controlling pelvic hemorrhage," by Vedantham et al., *American Journal of Obstetrics & Gynecology* April 1997, 176:4

"Uterine artery ligation in the control of postcesarean hemorrhage," by O'Leary, *J Reprod Med.* 1995 March; 40(3):189-93

"Uterine artery occlusion by embolization or surgery for the treatment of fibroids: a unifying hypothesis—transient uterine ischemia," by Burbank et al., *Journal of the American Association of Gynecologic Laparoscopists*, November 2007, Vol. 7, No. 4

"Vaginal ligature of uterine arteries during postpartum hemorrhage," by Philippe et al., International Journal of Gynecology and Obstetrics 56 (1997) 267-270

"Vaginal uterine artery ligation avoids high blood loss and puerperal hysterectomy in postpartum hemorrhage," by Hebisch et al., *OBSTETRICS & GYNECOLOGY* VOL. 100, NO. 3, SEPTEMBER 2002

SUMMARY OF THE INVENTION

For some applications of the present invention, a uterine artery compression device is used to occlude one or both of a subject's uterine arteries. The occlusion of the uterine artery is typically performed in order to reduce the supply of blood to a uterine fibroid, thereby causing irreversible ischemic necrosis and death of the fibroid. Typically, a fornix-engaging structure (e.g., a cervix cap) is inserted into the subject's vagina such that the structure engages the subject's vaginal fornix. First and second uterine artery compression devices, for example, occluding balloons, are inserted into the subject's body, via the fornix-engaging structure. The balloons are placed at sites outside of but in a vicinity of the left and right uterine arteries, respectively. The balloons are typically placed at sites that are posterior to the subject's broad ligament. When the balloons are at the sites, the balloons compress, and at least partially occlude, the uterine arteries by being inflated.

Typically prior to the occluding step, a positioning-anchoring balloon, disposed on the end of a positioning-anchoring tube, is inserted into the subject's uterus and inflated, such that the positioning-anchoring balloon stabilizes the occluding balloons. A blood flow monitoring system is used to monitor blood flow through the uterine arteries. For example, oximeters of the blood flow monitoring system may be disposed on the positioning-anchoring tube and used to detect when blood flow through the uterine arteries has stopped, by detecting a level of oxyhemoglobin in the vicinity of the uterine arteries.

For some applications, first and second rigid structures are inserted into left and right extrauterine positions anterior to the left and right broad ligaments. The left and right uterine artery compression devices compress the left and right uterine arteries by squeezing tissue against, respectively, the first and second rigid structures. For some applications, a single uterine artery compression device is placed at a site that is posterior to the broad ligament and the single uterine artery compression device squeezes both the left and right uterine arteries, respectively, against the left and right rigid structures.

For some applications, the compression device is coupled to the distal end of a rigid rod, which is typically hollow (i.e., it is a rigid tube), but for some applications is solid. Although some specific embodiments are described herein with respect to a rigid tube, it is noted that this is by way of illustration and not limitation, and the scope of the present invention includes use of a solid rod instead, unless context or explicit statement indicates otherwise. For example, the compression device may be a balloon that is disposed around the distal end of the rigid tube. The tube is inserted into the subject's body such that the distal end of the tube passes through vaginal tissue until the distal end of the tube is at a site ("the compression site") outside of the uterine artery of the subject, but in a vicinity of a portion of the uterine artery that supplies the uterine fibroid. When the distal end of the tube is at the site, the compression device compresses the artery. For example, the balloon is inflated such that the balloon compresses the artery. The rigidity of the tube typically ensures that the position of the distal end of the tube is maintained at the compression site during the compression of the artery. In this manner, as the balloon is inflated, the balloon exerts pressure on the uterine artery, rather than pushing the distal end of the tube away from the compression site.

Typically a fornix-engaging structure is inserted into the subject's vagina such that the structure engages the subject's fornix. The tube is inserted through the vaginal tissue, and the distal end of the tube is positioned at the compression site using a tube-guide that is coupled to the fornix-engaging structure. For some applications, the tube-guide is configured such that the tube is inserted into the subject's body at an angle that is not parallel to the longitudinal axis of the fornix-engaging structure. Typically, inserting the tube at such an angle facilitates placement of the distal end of the tube at the compression site. For some applications, the tube-guide is configured such that the tube is inserted into the subject's body parallel to the longitudinal axis of the fornix-engaging structure.

There is therefore provided, in accordance with some applications of the present invention, apparatus, for use with a subject's body, vagina, vaginal fornix, uterus, and uterine artery, the apparatus including:

a fornix-engaging structure configured to be inserted into the vagina and to engage the vaginal fornix;

a rod configured to be inserted into the subject's body via the fornix-engaging structure, such that a distal end of the rod passes through vaginal tissue at a first vaginal site until the distal end of the rod is at a first extrauterine site outside of the uterine artery, but in a vicinity of a portion of the uterine artery that supplies a uterine fibroid;

a rod-guide coupled to the fornix-engaging structure, and configured to guide the distal end of the rod to the first extrauterine site; and a uterine artery compression device disposed on the distal end of the rod.

For some applications, the rod is a hollow rod.

For some applications, the rod is a solid rod.

For some applications, the rod is shaped to prevent rotation of the rod with respect to the rod-guide.

For some applications, the fornix-engaging structure defines a longitudinal axis thereof, and the rod-guide is shaped to define a hole for guiding the rod, a longitudinal axis of the hole being parallel to the longitudinal axis of the fornix-engaging structure.

For some applications, the apparatus further includes a blood flow sensor configured to detect a change in blood flow through the uterine artery.

For some applications, the apparatus further includes a positioning-anchoring rod and a positioning-anchoring balloon disposed at a distal end of the positioning-anchoring rod, and:

the distal end of the positioning-anchoring rod is configured to be inserted into the subject's uterus, via a cervix of the subject, and the positioning-anchoring balloon is configured to anchor the uterine artery compression device while the uterine artery compression device is outside of the uterus, by the positioning-anchoring balloon being inflated while the distal end of the positioning-anchoring rod is inside the subject's uterus.

For some applications, the fornix-engaging structure and the rod-guide are coupled by being an integrated unit.

For some applications, the rod-guide is reversibly couplable to the fornix-engaging structure.

For some applications, the rod-guide is configured to be coupled to the fornix-engaging structure before the fornix-engaging structure is inserted into the subject's vagina.

For some applications, the rod-guide is configured to be coupled to the fornix-engaging structure when the fornix-engaging structure has engaged the vaginal fornix.

For some applications, the uterine artery compression device includes a balloon.

For some applications, the balloon is substantially not stretchable.

For some applications, the fornix-engaging structure defines a longitudinal axis thereof, and the rod-guide is shaped to define a hole for guiding the rod, a longitudinal axis of the hole not being parallel to the longitudinal axis of the fornix-engaging structure.

For some applications, an angle between the longitudinal axis of the rod-guide and the longitudinal axis of the hole is less than 60 degrees.

For some applications, the angle between the longitudinal axis of the rod-guide and the longitudinal axis of the hole is between 10 degrees and 45 degrees.

For some applications, the angle between the longitudinal axis of the rod-guide and the longitudinal axis of the hole is between 15 degrees and 30 degrees.

For some applications, the rod includes a rigid rod.

For some applications, the fornix-engaging structure and the rod-guide include rigid structures configured to maintain the distal end of the rod at the site by supporting the rod.

For some applications, the apparatus further includes a rigid positioning-anchoring rod and a positioning-anchoring balloon disposed at a distal end of the positioning-anchoring rod, and:

the distal end of the positioning-anchoring rod is configured to be inserted into the subject's uterus, via a cervix of the subject, and the positioning-anchoring balloon is configured to anchor the uterine artery compression device while the uterine artery compression device is outside of the uterus, by the positioning-anchoring balloon being inflated while the distal end of the positioning-anchoring rod is inside the subject's uterus.

For some applications, the uterine artery compression device is configured to compress the uterine artery by squeezing tissue of the subject against a portion of the apparatus.

For some applications, the uterine artery compression device is configured to compress the uterine artery by squeezing the subject's tissue against the fornix-engaging structure.

For some applications:

the rod includes first and second rods configured to be inserted into the subject's body, such that distal ends of the rods are at sites outside of but in a vicinity of left and right uterine arteries of the subject, respectively, and the uterine artery compression device includes left and right uterine artery compression devices disposed, respectively, on the distal end of the first and second rods, and configured to compress, respectively, the left and right uterine arteries by each uterine artery compression device squeezing tissue against the other uterine artery compression device.

For some applications, the apparatus further includes a positioning-anchoring rod and a positioning-anchoring balloon disposed at a distal end of the positioning-anchoring rod, and:

the distal end of the positioning-anchoring rod is configured to be inserted into the subject's uterus, the positioning-anchoring balloon is configured to anchor the uterine artery compression device while the uterine artery compression device is outside of the uterus, by the positioning-anchoring balloon being inflated while the distal end of the rod is inside the subject's uterus, and the uterine artery compression device is configured to compress the uterine artery by squeezing the subject's tissue against the positioning-anchoring rod.

For some applications, the apparatus further includes a positioning-anchoring rod and a positioning-anchoring balloon disposed at a distal end of the positioning-anchoring rod, and:

the distal end of the positioning-anchoring rod is configured to be inserted into the subject's uterus, the positioning-anchoring balloon is configured to anchor the uterine artery compression device while the uterine artery compression device is outside of the uterus, by the positioning-anchoring balloon being inflated while the distal end of the rod is inside the subject's uterus, and the uterine artery compression device is configured to compress the uterine artery by squeezing the subject's tissue against the positioning-anchoring balloon.

For some applications:

the rod includes first and second rods configured to be inserted into the subject's body, such that distal ends of the rods are at left and right first extrauterine sites outside of but in a vicinity of left and right uterine arteries of the subject, respectively, and the uterine artery compression device includes left and right uterine artery compression devices disposed, respectively, on the distal end of the first and second rods, and configured to compress, respectively, the left and right uterine arteries.

For some applications, the rod-guide is shaped to define at least one guiding portion at approximately a six o'clock position with respect to the subject's uterus, and is configured to guide the first and second rods through vaginal tissue at approximately the six o'clock position, via the at least one guiding portion.

For some applications, the rod-guide includes a first guiding portion configured to guide the distal end of the first rod to the left first extrauterine site, and a second guiding portion configured to guide the distal end of the second rod to the right first extrauterine site, and an angle defined by the first guiding portion of the rod-guide, a longitudinal axis of the rod-guide, and the second guiding portion of the rod-guide is less than 10 degrees.

For some applications, the rod-guide is shaped to define first and second guiding portions at approximately a three o'clock position and a nine o'clock position with respect to the uterus, the rod-guide is configured to guide the first rod through vaginal tissue at approximately the three o'clock position, via the first guiding portion, and the rod-guide is configured to guide the second rod through vaginal tissue at approximately the nine o'clock position, via the second guiding portion.

For some applications, the rod-guide includes a first guiding portion configured to guide the distal end of the first rod to the left first extrauterine site, and a second guiding portion configured to guide the distal end of the second rod to the right first extrauterine site, and an angle defined by the first guiding portion of the rod-guide, a longitudinal axis of the rod-guide, and the second guiding portion of the rod-guide is between 170 and 190 degrees.

For some applications, the apparatus further includes a rigid structure configured to be inserted into the subject's body via the fornix-engaging structure, such that a distal end of the rigid structure passes through vaginal tissue at a second vaginal site, until the distal end of the rigid structure is at a second extrauterine site outside of the uterine artery, and the uterine artery compression device is configured to compress the uterine artery by squeezing tissue of the subject against the rigid structure.

For some applications, the rigid structure includes a curved distal portion thereof.

For some applications, a distal portion of the rigid structure is substantially straight.

For some applications, the rod and the rigid structure are pivotally connected to each other.

For some applications:

the rod includes first and second rods configured to be inserted into the subject's body, such that distal ends of the rods are at a first pair of extrauterine sites outside of but in a vicinity of left and right uterine arteries of the subject, respectively, the uterine artery compression device includes left and right uterine artery compression devices disposed, respectively, on the distal end of the first and second rods, the rigid structure includes left and right rigid structures configured to be inserted into the subject's body via the fornix-engaging structure, such that the distal ends of the rigid structures are at a second pair of extrauterine sites outside of but in a vicinity of left and right uterine arteries of the subject, respectively, the left uterine artery compression device is configured to compress the left uterine artery by squeezing tissue of the subject against the left rigid structure, and the right uterine artery compression device is configured to compress the right uterine artery by squeezing tissue of the subject against the right rigid structure.

For some applications:

the rigid structure includes left and right rigid structures configured to be inserted into the subject's body via the fornix-engaging structure, such that the distal ends of the rigid structures are at second extrauterine sites outside of but in a vicinity of left and right uterine arteries of the subject, respectively, and the uterine artery compression device includes a single uterine artery compression device that is configured to:

compress the left uterine artery by squeezing tissue of the subject against the left rigid structure, and compress the right uterine artery by squeezing tissue of the subject against the right rigid structure.

For some applications, the rod-guide includes a first guiding portion configured to guide the distal end of the rod to the first extrauterine site, and a second guiding portion configured to guide the distal end of the rigid structure to the second extrauterine site, and an angle defined by the first guiding portion of the rod-guide, a longitudinal axis of the rod-guide, and the second guiding portion of the rod-guide is greater than 100 degrees.

For some applications, the rod-guide includes a first guiding portion configured to guide the distal end of the rod to a first extrauterine site that is posterior to a broad ligament of the subject, and a second guiding portion configured to guide the distal end of the rigid structure to a second extrauterine site that is anterior to the broad ligament.

For some applications, the rigid structure includes a rigid solid rod.

For some applications, the rigid structure includes a rigid hollow rod.

For some applications, the apparatus further includes a balloon disposed on the distal end of the rigid structure.

For some applications, the balloon is substantially not stretchable.

For some applications:
the rod-guide defines at least one guiding portion at approximately a position with respect to the subject's uterus, selected from the group consisting of: a 2 o'clock position, a 3 o'clock position, a 6 o'clock position, a 9 o'clock position, and a 10 o'clock position, and
the rod-guide is configured to guide the rod and the rigid structure through vaginal tissue, via the at least one guiding portion.

For some applications:
the rod-guide includes (a) a first guiding portion at approximately a 6 o'clock position with respect to the subject's uterus, and (b) a second guiding portion at approximately a position with respect to the subject's uterus selected from the group consisting of: a 2 o'clock position and a 10 o'clock position,
the rod-guide is configured to guide the rod through vaginal tissue at approximately the 6 o'clock position, via the first guiding portion, and
the rod-guide is configured to guide the rigid structure through vaginal tissue at approximately the selected position, via the second guiding portion.

For some applications:
the rod-guide defines a first guiding portion at approximately a 2 o'clock position with respect to the subject's uterus, a second guiding portion at approximately a 10 o'clock position with respect to the subject's uterus, and a third guiding portion at approximately a 6 o'clock position with respect to the subject's uterus,
the rigid structure includes left and right rigid structures,
the rod-guide is configured to guide the left rigid structure through vaginal tissue at approximately the 2 o'clock position, via the first guiding portion,
the rod-guide is configured to guide the right rigid structure through vaginal tissue at approximately the 10 o'clock position, via the second guiding portion, and
the rod-guide is configured to guide the rod through vaginal tissue at approximately the 6 o'clock position, via the third guiding portion.

There is further provided, in accordance with some applications of the present invention, apparatus, including:
a rod having a telescoping distal portion thereof, and a longitudinal axis thereof; and
a balloon disposed around the telescoping portion,
the apparatus being such that when the balloon is in an inflated state thereof, the rod is configured to increase a diameter of the balloon in a direction that is perpendicular to the longitudinal axis of the rod, by the telescoping portion of the rod being shortened.

For some applications, the rod is a hollow rod.

For some applications, the rod is a solid rod.

For some applications, the rod is configured to be inserted into a subject's body, such that a distal end of the rod passes through vaginal tissue, until the distal portion of the rod is at a site outside of a uterine artery of the subject, but in a vicinity of a portion of the uterine artery that supplies a uterine fibroid.

For some applications, the balloon is configured to at least partially occlude the uterine artery by being inflated while the distal portion is at the site.

For some applications, the balloon is configured to further occlude the uterine artery by the telescoping portion of the rod being shortened while the distal portion is at the site.

There is additionally provided, in accordance with some applications of the present invention, apparatus, including:
a measuring device configured to measure a parameter that is indicative of a level of blood-flow through blood vessels of a subject;
an output unit; and
a control unit configured to drive the output unit to generate an output that is (a) indicative of blood flow through a portion of one of the blood vessels having stopped due to (b) the parameter having changed and then plateaued at a value indicating non-zero blood flow in a vicinity of the blood vessels.

For some applications, the measuring device is configured to be placed in a vicinity of a uterine artery of the subject, and the control unit is configured to drive the output unit to generate an output that is (a) indicative of blood flow through a portion of the uterine artery having stopped due to (b) the parameter having changed and then plateaued at a value indicating non-zero blood flow in the vicinity of the uterine artery.

For some applications, the measuring device includes a pressure sensor configured to detect pressure in the vicinity of the blood vessels, and the control unit is configured to drive the output unit to generate an output that is indicative of a strength of a pulsating component of the detected pressure having decreased and then plateaued at a value indicating non-zero blood flow in the vicinity of the blood vessels.

For some applications, the measuring device includes a microphone configured to detect sound waves in the vicinity of the blood vessels, and the control unit is configured to drive the output unit to generate an output that is indicative of a strength of a pulsating component of the detected sound waves having decreased and then plateaued at a value indicating non-zero blood flow in the vicinity of the blood vessels.

For some applications, the measuring device includes a spectrometer.

For some applications, the measuring device includes an oximeter.

There is further provided, in accordance with some applications of the present invention, apparatus for use with a subject's uterus, including:
a rod, a distal end of which is configured to be inserted into the subject's uterus;
a balloon disposed on the distal end of the rod and configured to be inflated while the distal end of the rod is inside the subject's uterus; and
an oximeter disposed on the distal end of the rod and configured to detect a change in blood flow in a vicinity of the uterus by measuring a level of oxyhemoglobin in the vicinity while the distal end of the rod is inside the subject's uterus.

For some applications, the rod is hollow.

For some applications, the rod is solid.

There is further provided, in accordance with some applications of the present invention, apparatus, including:

a medical tool configured to be placed inside a body of a subject, outside of a reproductive tract of the subject; and a positioning-anchoring balloon coupled to the tool, and configured to stabilize the tool by being inserted into a uterus of the subject and engaging the subject's uterus by the balloon being inflated.

For some applications, the medical tool includes a uterine artery compression device.

There is additionally provided, in accordance with some applications of the present invention, apparatus, for use with a subject's body, uterus, vagina and uterine artery, the apparatus including:

a guide structure having a first guiding portion at a site that is at approximately a 6 o'clock position with respect to the subject's uterus, and a second guiding portion that is approximately at a position with respect to the subject's uterus selected from the group consisting of: a 2 o'clock position and a 10 o'clock position, a first compression device, the guide structure being configured to guide the first compression device into the subject's body, via a vaginal site of the vagina that is at approximately the 6 o'clock position, via the first guiding portion, and a second compression device, the guide structure being configured to guide the second compression device into the subject's body, via a vaginal site of the vagina that is at approximately at the selected position, via the second guiding portion the first and second compression devices being configured to compress the uterine artery by each compression device squeezing tissue against the other compression device.

There is further provided, in accordance with some applications of the present invention, apparatus, for use with a subject's vagina and uterine artery, the apparatus including:

first and second balloons configured to:

be inserted into the subject's body, via at least one vaginal site of the vagina, and compress the uterine artery by each balloon squeezing tissue against the other balloon.

For some applications, one of the first and second balloons is substantially not stretchable, and another one of the first and second balloons is substantially stretchable.

For some applications, the apparatus further includes a pressure sensor configured to detect pressure in a vicinity of the balloons by detecting pressure inside the balloon that is substantially not stretchable.

There is further provided, in accordance with some applications of the present invention, a method, for use with a subject's body, vagina, vaginal fornix, uterus, and uterine artery, the method including:

engaging the vaginal fornix with a fornix-engaging structure, by inserting the structure into the vagina;

inserting a rod into the subject's body via the fornix-engaging structure;

using a rod-guide, guiding the rod such that a distal end of the rod passes through vaginal tissue at a first vaginal site until the distal end of the rod is at a first extrauterine site outside of the uterine artery, but in a vicinity of a portion of the uterine artery that supplies a uterine fibroid; and while the distal end of the rod is at the site, compressing the uterine artery using a uterine artery compression device disposed on the distal end of the rod.

For some applications, the method further includes positioning and anchoring the uterine artery compression device while the uterine artery compression device is at the site, by placing a positioning-anchoring balloon inside the uterus and inflating the positioning-anchoring balloon while the positioning-anchoring balloon is inside the uterus.

For some applications, inserting the rod into the subject's body includes inserting a rigid rod into the subject's body, and compressing the uterine artery using the uterine artery compression device disposed on the distal end of the rod, includes maintaining the position of the distal end of the rod at the site, using the rigidity of the rod.

For some applications:

the rod includes left and right rods, and the uterine artery compression device includes left and right uterine artery compression devices disposed, respectively, on distal ends of the left and right rods, guiding the rod includes guiding the left and right rods, via left and right first vaginal sites, such that distal ends of the rods are at left and right first extrauterine sites outside of but in a vicinity of left and right uterine arteries of the subject, respectively, and compressing the uterine artery includes compressing the left and right uterine arteries, using, respectively, the left and right uterine artery compression devices.

For some applications, guiding the left and right rods includes guiding the rods to the left and right first extrauterine sites via vaginal tissue at approximately a six o'clock position with respect to the subject's uterus.

For some applications, guiding the left rod includes guiding the left rod to the left first extrauterine site via vaginal tissue at approximately a three o'clock position with respect to the subject's uterus, and guiding the right rod includes guiding the right rod to the right first extrauterine site via vaginal tissue at approximately a nine o'clock position with respect to the subject's uterus.

For some applications, the method further includes inserting a rigid structure into the subject's body via the fornix-engaging structure, such that a distal end of the rigid structure passes through vaginal tissue at a second vaginal site, until the distal end of the rigid structure is at a second extrauterine site outside of the uterine artery, and compressing the uterine artery using the uterine artery compression device includes compressing the uterine artery by squeezing tissue of the subject against the rigid structure, using the uterine artery compression device.

For some applications, guiding the rod such that the distal end of the rod is at the first extrauterine site includes guiding the rod such that the distal end of the rod is at an extrauterine site that is posterior to a broad ligament of the subject, and guiding the rigid structure such that the distal end of the rigid structure is at the second extrauterine site includes guiding the distal end of the rigid structure to a second extrauterine site that is anterior to the broad ligament of the subject.

There is further provided, in accordance with some applications of the present invention, a method, including:

providing a rod having a telescoping distal portion thereof, a longitudinal axis thereof, and a balloon disposed around the telescoping portion;

inflating the balloon; and while the balloon is in a subject's body, shortening the telescoping portion of the rod.

There is additionally provided, in accordance with some applications of the present invention, a method, including:

placing a measuring device in a vicinity of a plurality of blood vessels of a subject;

using the measuring device, measuring a parameter that is indicative of a level of blood-flow through the blood vessels; and determining that blood flow through one of the blood vessels has stopped by detecting that the parameter has changed and then plateaued at a value indicating non-zero blood flow in the vicinity of the blood vessels.

There is further provided, in accordance with some applications of the present invention, a method for use with a subject's uterus, including:

inserting a distal end of an elongate element into the subject's uterus;

inflating a balloon disposed on the distal end of the elongate element, while the distal end of the elongate element is inside the subject's uterus; and detecting a change in blood flow in a vicinity of the uterus by measuring a level of oxyhemoglobin in the vicinity using an oximeter that is disposed on the distal end of the elongate element, while the distal end of the elongate element is inside the subject's uterus.

There is additionally provided, in accordance with some applications of the present invention, a method, including:

inserting a device inside a body of a subject, and outside of a uterus of the subject; and anchoring the device by inserting a balloon into the subject's uterus and engaging the subject's uterus with the balloon by inflating the balloon, the balloon being coupled to the device.

There is further provided, in accordance with some applications of the present invention, a method for compressing a uterine artery of a subject, including:

placing a first compression device at an extrauterine site that is posterior to a broad ligament of the subject;

placing a second compression device at an extrauterine site that is anterior to the broad ligament of the subject; and compressing the uterine artery by squeezing tissue between the first and second compression devices.

For some applications, compressing the uterine artery includes avoiding occluding ureters of the subject.

There is additionally provided, in accordance with some applications of the present invention, a method for compressing a uterine artery of a subject, including:

providing a balloon having a first side and a second side, the first side being more flexible than the second side; and compressing the uterine artery by:
 placing the balloon such that the first side of the balloon faces the uterine artery; and
 causing the balloon to expand at least in the direction of the uterine artery, by inflating the balloon.

There is further provided, in accordance with some applications of the present invention, a method, including:

providing left and right uterine artery compression devices coupled to each other by a flexible material; and occluding left and right uterine arteries of a subject using, respectively, the left and right uterine artery compression devices.

For some applications, the flexible material defines a maximum distance between respective centers of the left and right uterine artery compression devices, and providing the left and right uterine artery compression devices includes providing the devices such that that the maximum distance is 5-25 cm.

For some applications, occluding includes inflating the uterine artery compression devices.

For some applications, occluding includes squeezing at least one of the uterine arteries between (a) apparatus placed into the subject and (b) one of the compression devices.

The present invention will be more fully understood from the following detailed description of embodiments thereof, taken together with the drawings, in which:

BRIEF DESCRIPTION OF THE DRAWINGS

FIGS. 3A-F are schematic illustrations of the device of FIG. 2, in accordance with some applications of the present invention;

DETAILED DESCRIPTION OF EMBODIMENTS

Figure 1:
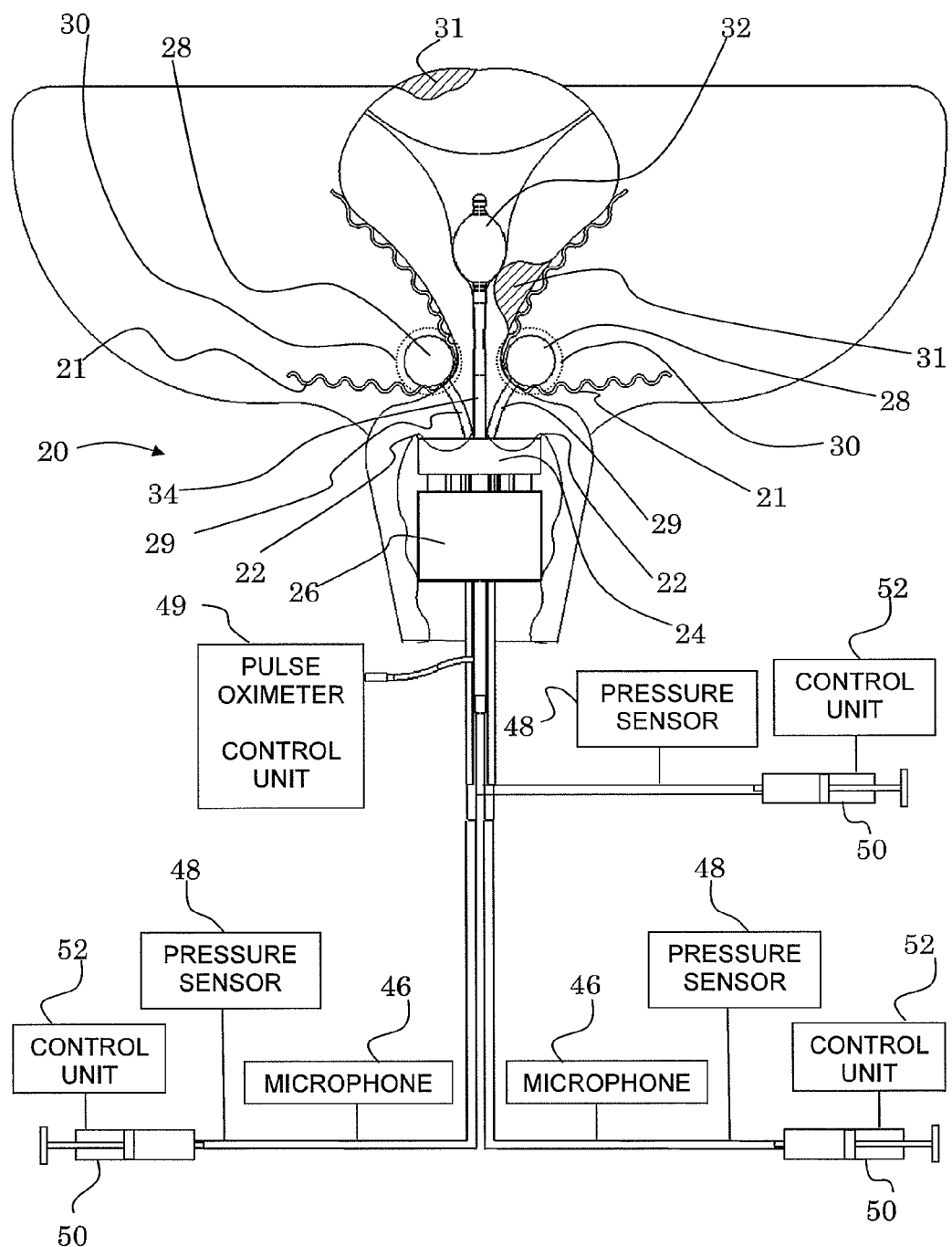
FIG. 1 is a schematic illustration of a device configured to at least partially occlude a subject's uterine arteries, in accordance with some applications of the present invention.

Reference is now made to FIG. 1, which is a schematic illustration of a device 20 configured to at least partially occlude a subject's uterine arteries 21, in accordance with some applications of the present invention. The occlusion of the uterine arteries is typically performed in order to reduce the supply of blood to uterine fibroids 31, thereby causing irreversible ischemic necrosis and death of the fibroids.

Typically, a fornix-engaging structure 24 is inserted into the subject's vagina. Subsequently, an incision 22 is made in the vaginal wall. (Although the incision in the vaginal wall is shown at 3 o'clock and 9 o'clock positions, for some applications, incision 22 is made at other positions on the vaginal wall, for example, at a 6 o'clock, a 2 o'clock, and/or a 10 o'clock position, as described in further detail hereinbelow.) A guide structure 26 is coupled to fornix-engaging structure 24. A uterine artery compression device, for example, a balloon 28 (as shown), is disposed on the distal end of a tube 29. (For some applications, as described hereinabove, a solid rod is used in place of tube 29 (i.e., a hollow rod), mutatis mutandis). The tube is inserted into the subject's body, and the tube-guide guides the tube such that the distal end of the tube passes through vaginal tissue until the distal end of the tube is at a site 30 that is adjacent to the subject's cervix, e.g., above the subject's fornix, and below the subject's uterus. Site 30 is typically outside of uterine artery 21, but in a vicinity of a portion of the uterine artery that supplies uterine fibroid 31. The tube is typically inserted via incision 22. While the distal end of the tube is at site 30, the uterine compression device is used to compress, and at least partially occlude the subject's uterine artery. For example, while the distal end of the tube is at site 30, the balloon is inflated in order to occlude the uterine artery.

Typically, the distal end of tube 29 is blunt, for applications in which tube 29 is inserted via incisions that have previously been made in the vaginal tissue, as described hereinabove. For some applications, the distal end of tube 29 is sharp, and is used to penetrate the vaginal tissue by forming incisions in the vaginal tissue. For some applications, in order to prevent the sharp distal end of tube 29 from damaging tissue in the vicinity of the tube, the sharp distal end is folded subsequent to the penetration of the vaginal tissue by the distal end of the tube. For some applications, techniques that are known in the art (such as those that are used with laparoscopic tools) are used for folding the sharp distal end of the tube.

Figure 4A:
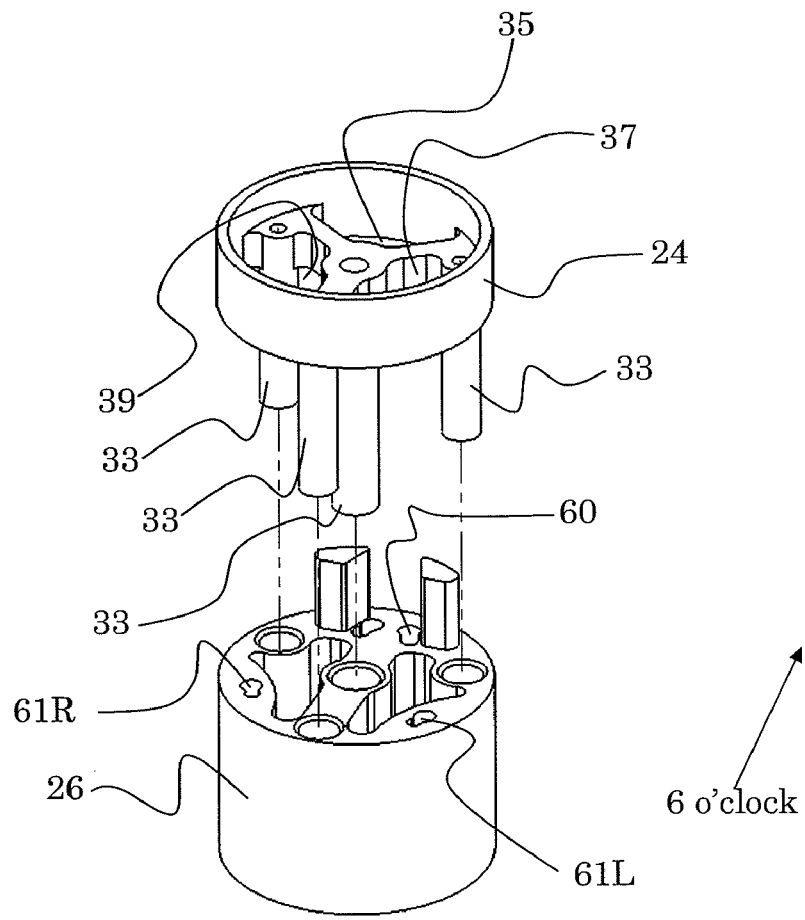
FIGS. 4A-B are schematic illustrations of a tube-guide, in accordance with some applications of the present invention.

For some applications, tube-guide 26 and fornix-engaging structure 24 form a single integrated unit. Alternatively, the tube-guide and the fornix-engaging structure are reversibly couplable to each other (e.g., as shown in FIG. 4A). For some applications, tube 29 is inserted into the subject's body, via the fornix-engaging structure, prior to the tube-guide being coupled to the fornix-engaging structure. Subsequently, the tube-guide is coupled to the fornix-engaging structure, thereby guiding the distal end of the tube-guide to site 30. Typically, for such applications, prior to the tube-guide being coupled to the fornix-engaging structure, tube 29 is able to rotate with respect to the fornix-engaging structure. For example, as seen in FIG. 4A, the size of hole 35 in the fornix-engaging structure (through which the tube is inserted) is substantially larger than the cross-section of the tube. After the tube-guide has subsequently been coupled to the fornix-engaging structure, the tube is inhibited by the tube-guide from rotating with respect to the fornix-engaging structure. Typically, the shape and size of hole 60 (shown in FIG. 4A) in the tube-guide through which the tube is inserted is substantially similar to the cross-section of the tube.

For some applications (as shown), left and right balloons are inserted into sites 30 on, respectively, the left and right side of the subject's cervix. The balloons are used to compress, and at least partially occlude, left and right uterine arteries of the subject, in accordance with the techniques described herein. Typically, the left and right arteries are compressed simultaneously. Alternatively the left and right arteries are compressed at separate times. For some applications, apparatus and methods that are described herein, as being applied to a single uterine artery are applied to left and right uterine arteries, at least partially, simultaneously.

Figure 2:
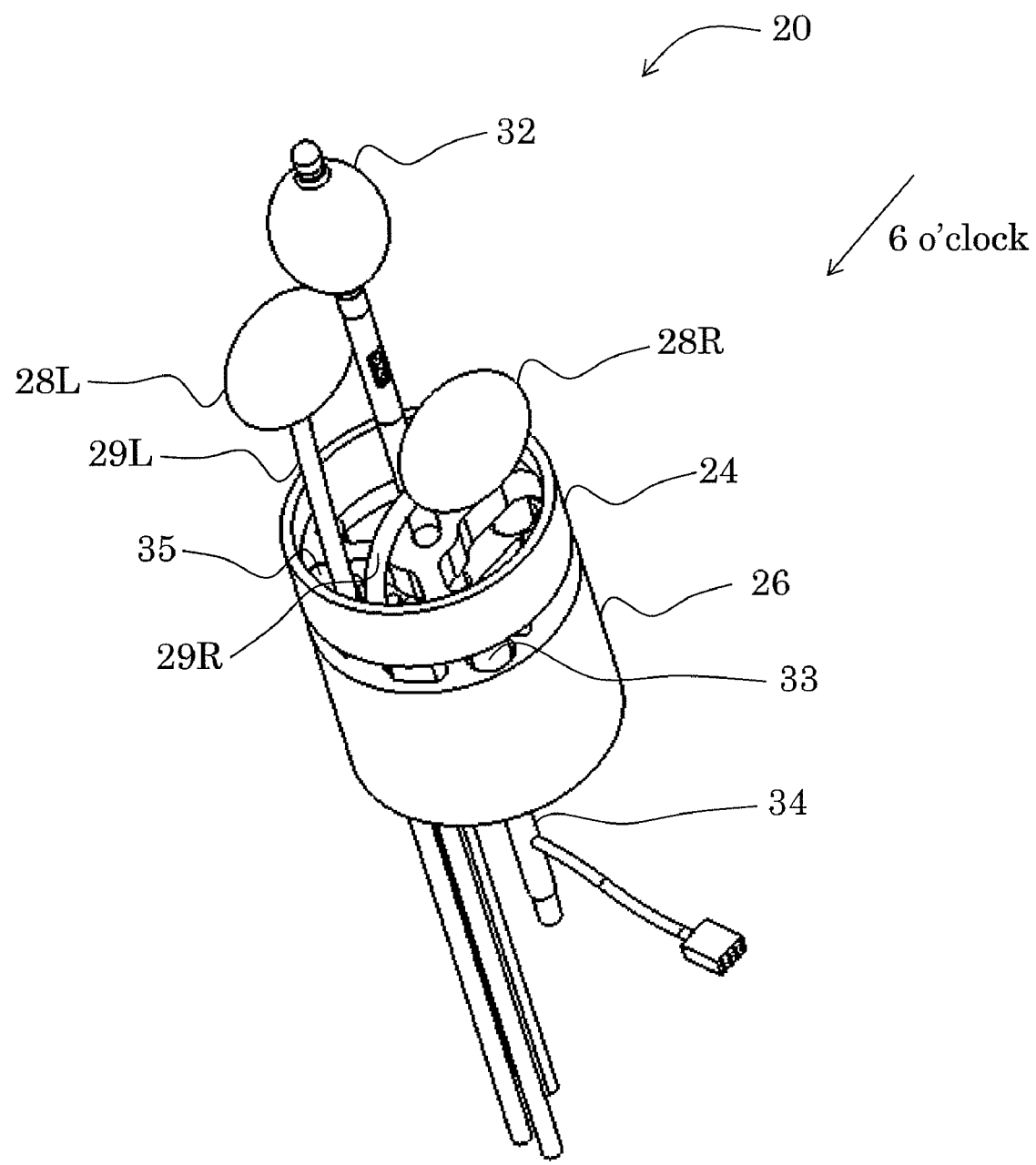
FIG. 2 is a schematic illustration of the device, in accordance with some applications of the present invention.

For some applications, a single (posterior) incision is made at the 6 o'clock position of the fornix (i.e., the posterior fornix), and left and right balloons 28 are inserted via the single incision. Device 20, as used for such applications, is shown in FIGS. 2-4. Alternatively, left and right balloons 28 are inserted into sites 30 on the left and right side of the subject's cervix via incisions 22 at approximately 3 o'clock and 9 o'clock positions of the fornix (i.e., the lateral fornix) with respect to the subject's uterus. Device 20, as used for such applications, is shown in FIGS. 5 and 6A-C.

For some applications, a positioning-anchoring balloon 32, disposed at the distal end of a positioning-anchoring tube 34 is inserted into the subject's uterus, via the subject's cervix. (For some applications, a solid rod is used in place of tube 34 (which is a hollow rod), mutatis mutandis.) The intrauterine positioning-anchoring balloon is inflated while it is disposed in the uterus, in order to position and then anchor device 20. For example, balloon 32 may be used to position and anchor extrauterine compression balloons 28 with respect to the subject's cervix and uterine arteries. For some applications, a balloon that is similar to the silicone balloon of The Rumi System® is used as the intrauterine balloon. For some applications, the length of the positioning-anchoring tube with respect to the fornix-engaging structure is adjustable. For example, the positioning-anchoring tube may be threadedly coupled to the fornix-engaging structure and/or the tube-guide, such that the height of the positioning-anchoring tube with respect to the fornix-engaging structure is controlled by screwing the positioning-anchoring tube through the fornix-engaging structure and/or the tube-guide.

For some applications, uterine artery 21 is compressed due to each of left and right balloons 28 squeezing (i.e., forcing) tissue toward the other balloon. Alternatively or additionally, one or both of balloons 28 squeeze tissue against positioning-anchoring tube 34, and/or positioning-anchoring balloon 32. For some applications, one or both of balloons 28 squeeze tissue against fornix-engaging structure 24. For some applications, balloon 28 compresses the uterine artery by generally causing compression of tissue in the vicinity of the balloon, and without squeezing the subject's tissue against another portion of device 20.

Figure 3B:
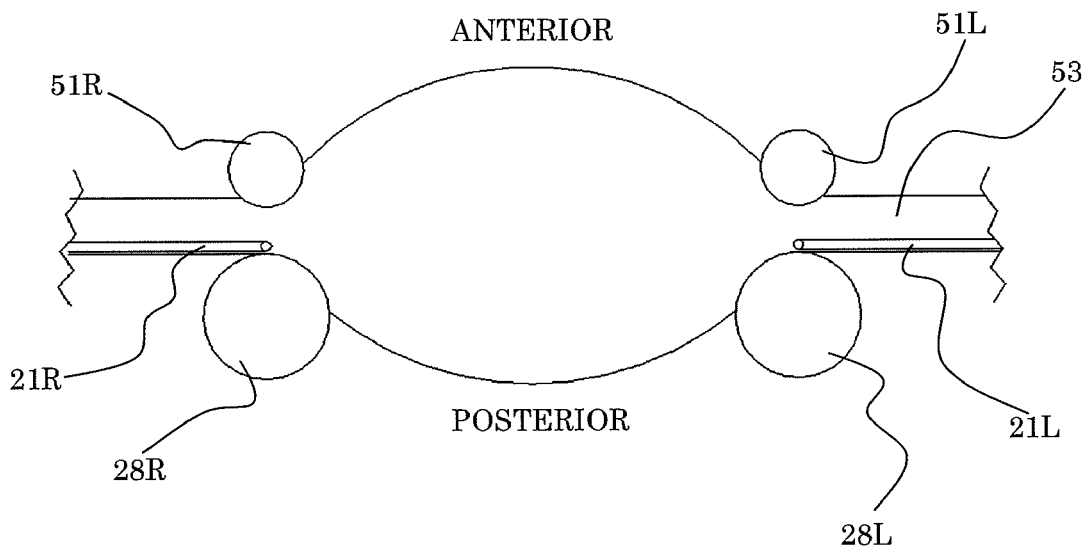
Figure 3C:
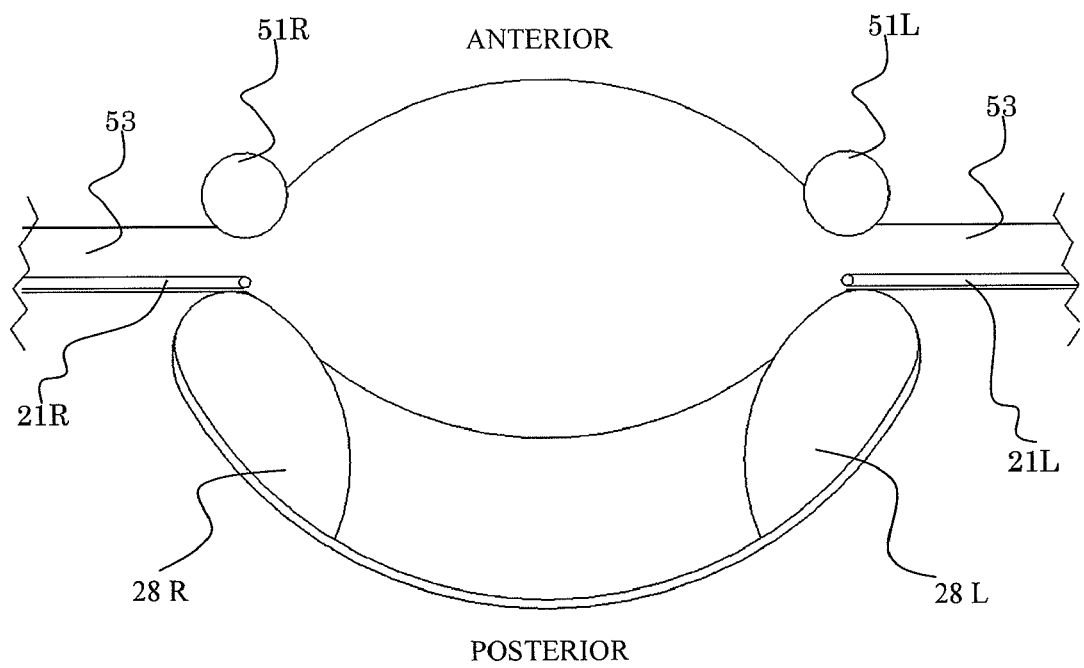

For some applications, first and second rigid structures 51 are inserted into left and right extrauterine positions anterior to the left and right broad ligaments (as shown in FIG. 3B). For some applications, rigid structures 51 are uterine artery compression devices. The left and right uterine artery compression devices 28 are inserted into left and right extrauterine positions posterior to the left and right broad ligaments. The left and right uterine artery compression devices 28 compress the left and right uterine arteries by squeezing tissue against, respectively, the first and second rigid structures. For some applications, a single uterine artery compression device is placed at a site that is posterior to the broad ligament and the single uterine artery compression device squeezes both the left and right uterine arteries, respectively, against the left and right rigid structures (as shown in FIG. 3C).

Typically, tube 29 is a rigid tube. The rigidity of the tube maintains the position of the distal end of the tube at site 30, while balloon 28 is inflated and compresses the uterine artery. (If tube 29 were not rigid, then some of the inflation of the balloon would be in effect wasted. In some cases, this might cause the tube to bend away from the uterine artery, such that the balloon does not have sufficient compressive effect to occlude the uterine arteries.) For some applications, tube 29 is flexible, for example, during insertion of the tube through the vagina, but becomes rigid for compressing the uterine artery. Typically, fornix-engaging structure 24, tube-guide 26, and positioning-anchoring tube 34 are also rigid.

Reference is now made to FIG. 2, which is a schematic illustration of device 20, in accordance with some applications of the present invention. For some applications, a single incision is made in the vaginal tissue at approximately the 6 o'clock position, and left and right tubes 29 and balloons 28 are inserted via the single incision. Tube-guide 26 defines two holes 60 (shown in FIG. 4A) at approximately the 6 o'clock position. Tubes 29L and 29R are both inserted through the incision in the vaginal tissue at the 6 o'clock position by fornix-engaging structure 24 being pushed against the subject's fornix, and the tubes being inserted through a hole 35 in structure 24.

For some applications, subsequent to the fornix-engaging structure being pushed against the fornix, and/or subsequent to tubes 29 having been inserted through hole 35 in structure 24, tube-guide 26 is coupled to structure 24 via coupling elements 33. The tube-guide guides left and right tubes 29L and 29R to their respective positions, by being coupled to the fornix-engaging structure. As shown in FIG. 3B, the distal ends of tubes 29L and 29R are appropriately shaped for balloons 28L and 28R to be positioned adjacent to left and right uterine arteries 21L and 21R posterior to broad ligaments 53 by being inserted through the incision at the 6 o'clock position.

Reference is now made to FIGS. 3A-E, which are schematic illustrations of device 20 including rigid structures 51, in accordance with some applications of the invention. For some applications, rigid structures are solid rods, or hollow rods (i.e., tubes). For some applications, in addition to an incision being made in the vaginal tissue at approximately the 6 o'clock position (as described with reference to FIG. 2), incisions are made at approximately the 2 o'clock and 10 o'clock positions of the vaginal fornix. Left rigid structure 51L is inserted to an extrauterine site that is anterior to the broad ligament in the vicinity of left uterine artery 21L (shown in FIG. 3B), via the 2 o'clock incision. Alternatively or additionally, right rigid structure 51R is inserted to an extrauterine site that is anterior to the broad ligament in the vicinity of right uterine artery 21R (also shown in FIG. 3B), via the 10 o'clock incision. Left and right extrauterine sites of the left and right rigid structures are typically anterior to, respectively, the subject's left and right broad ligaments 53. Typically, as with tube 29, left and right rigid structures 51*l* and 51R are inserted into the subject's body via fornix-engaging structure 24. Subsequently, tube-guide 26 is coupled to the fornix-engaging structure and guides the rigid structures to their respective sites.

For some applications, uterine artery compression device 28 includes left and right uterine artery compression devices 28L and 28R. The left uterine artery compression device compresses left uterine artery 21L, by squeezing the subject's broad ligament and the uterine artery against left rigid structure 51L, as shown in FIG. 3B. The right uterine artery compression device compresses right uterine artery 21R, by squeezing the subject's broad ligament and the uterine artery against right rigid structure 51R, also as shown in FIG. 3B. The compression of the uterine arteries is thus performed in an anterior-posterior direction, and not in a lateral direction. For some applications, by performing the uterine artery compression in the anterior-posterior direction, occlusion of the subject's ureters is reduced or avoided. Alternatively, for some applications, the subject's uterine arteries are compressed in a lateral direction. Typically, using rigid structures 51L and 51R in addition to the uterine artery compression device facilitates compression of the uterine arteries, as the rigid structures provide resistance against which to push the uterine arteries. Typically, inserting the rigid structures at the 2 o'clock and 10 o'clock positions ensures that the rigid structures are inserted to sites that are anterior to the broad ligaments.

Figure 3D:
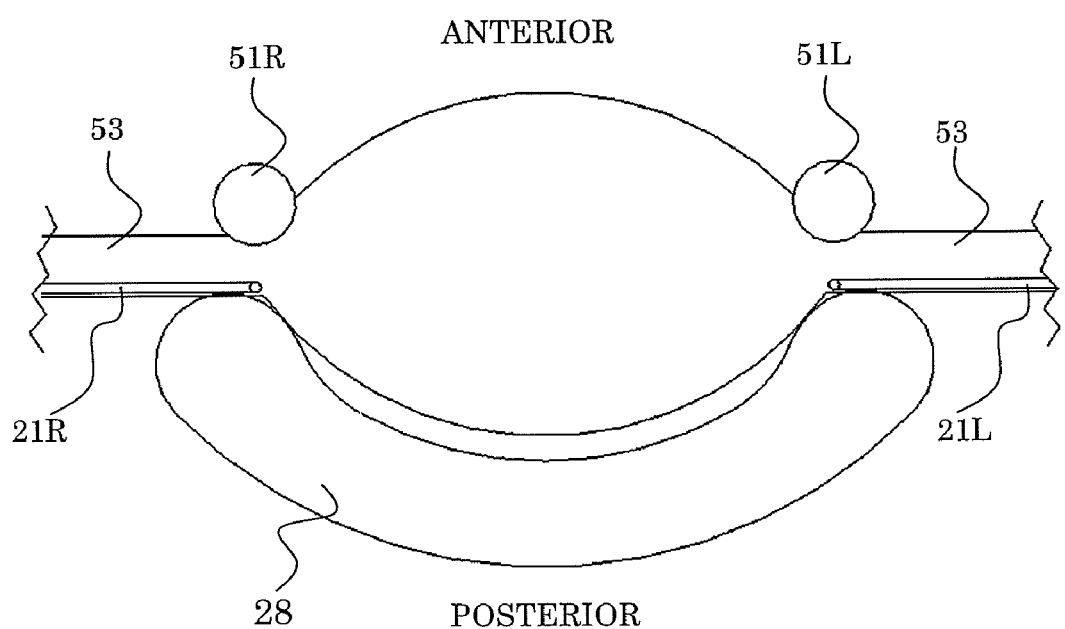

For some applications, left and right uterine artery compression devices 28 are balloons that are coupled to a flexible backing material 74, as shown in FIG. 3C, and as described in detail with reference to FIG. 8C. For some applications, uterine artery compression device 28 is a single uterine artery compression device, for example a curved balloon, as shown in FIG. 3D. The uterine artery compression device compresses left and right uterine arteries by squeezing the broad ligament and the uterine arteries against, respectively, left and right rigid structure 51L and 51R.

Figure 3E:
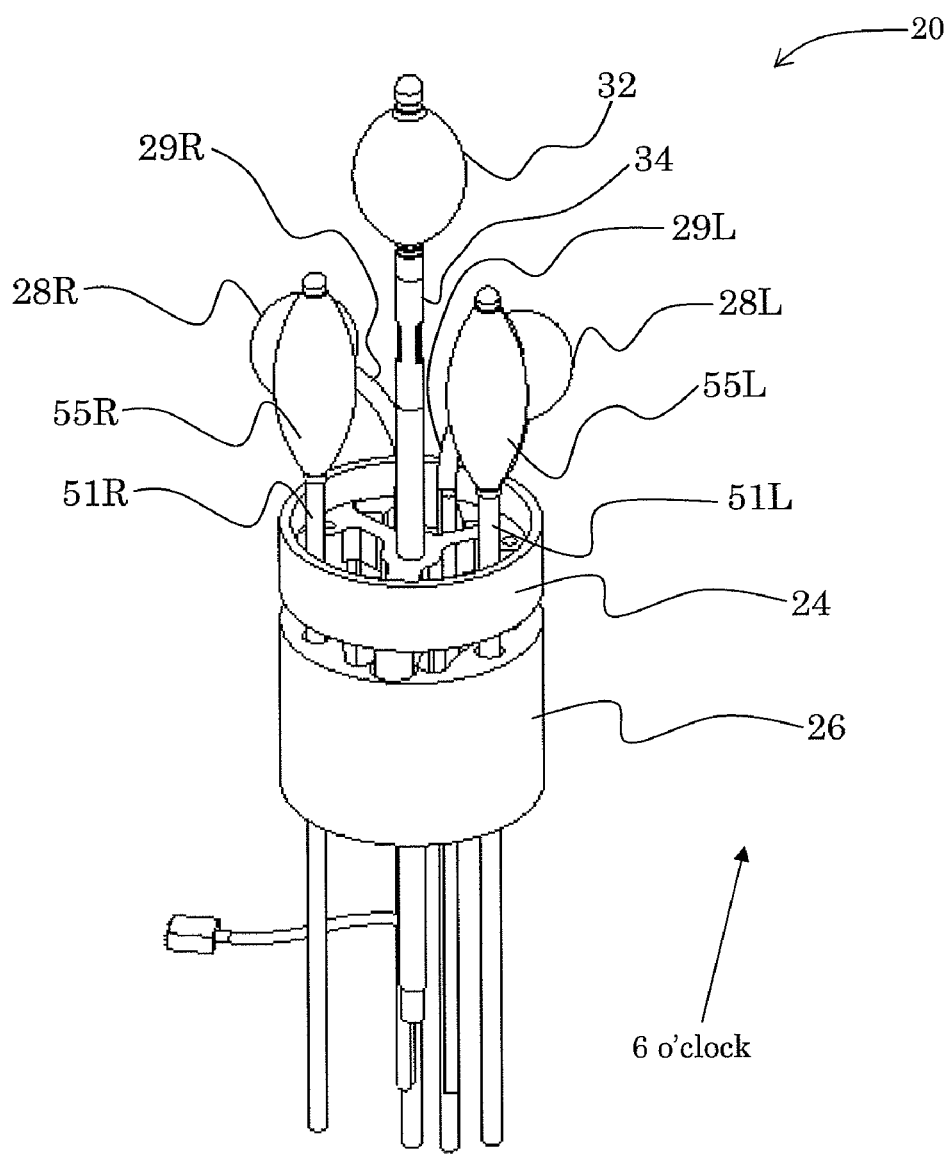
Figure 3F:
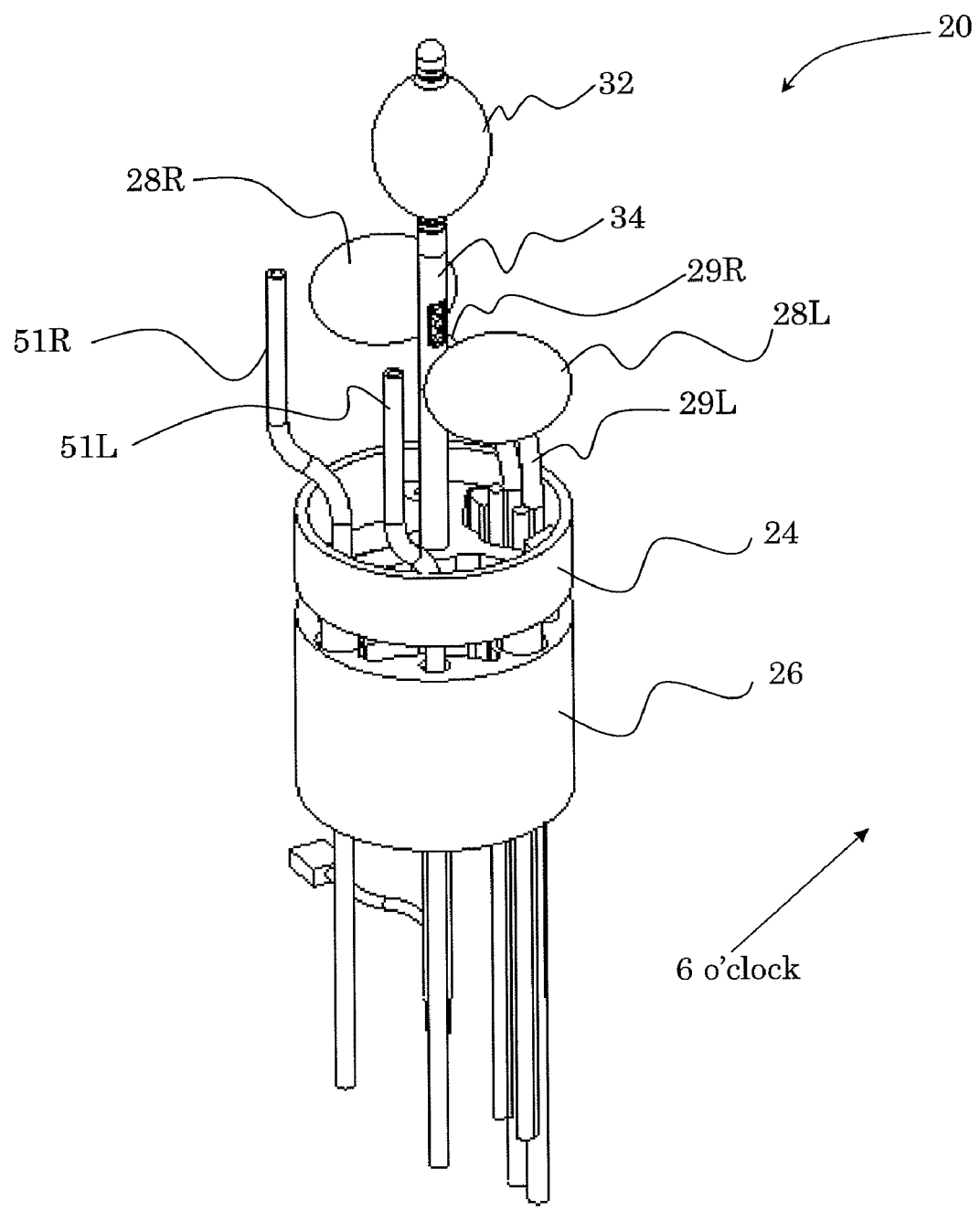

For some applications, balloons 55L and 55R are disposed on the distal ends of, respectively, rigid structure 51L and rigid structure 51R, as shown in FIG. 3E. Typically the balloons facilitate compression of the uterine arteries, and/or facilitate measurement of the pressure in the vicinity of the uterine arteries, as described in further detail hereinbelow. For some applications, balloons 55 are uterine artery compression devices. For some applications, distal portions of rigid structures 51L and 51R are curved, as shown in FIG. 3F, to facilitate insertion of the structures to suitable extrauterine sites. Alternatively, the distal portions of the rigid structures are substantially straight, as shown in FIG. 3A. For some applications, left rigid structure 51L and left tube 29L are pivotally connected to each other, e.g., structure 51L and tube 29L may comprise a clamp (pivot not shown). Similarly, for some applications, right rigid structure 51R and right tube 29R are pivotally connected to each other. For example, left rigid structure 51L and left tube 29L, and/or right rigid structure 51R and right tube 29R, act as a hemostat.

Reference is now made to FIGS. 3A-F and to FIG. 4A, FIG. 4A being a schematic illustration of fornix-engaging structure 24 and tube-guide 26 in a decoupled state, in accordance with an application of the present invention. For some applications, device 20 is placed inside the subject's body in accordance with the following procedure:

(1) Positioning-anchoring tube 34 and positioning-anchoring balloon 32 are coupled to fornix-engaging structure 24.

(2) Before or after step (1), fornix-engaging structure 24 is inserted into the subject's vagina such that it engages the subject's fornix, and such that the distal end of positioning-anchoring tube 34 and the balloon 32 are placed inside the subject's uterus, via the subject's cervix.

(3) Positioning-anchoring balloon 32 is inflated so as to position and anchor the fornix-engaging structure.

(4) Incisions are made in the fornix (a) at the 6 o'clock position, via hole 35, (b) at the 2 o'clock position, via a hole 37, and (c) at the 10 O'clock position, via a hole 39.

(5) Left and right tubes 29 are inserted into the extrauterine space inside the subject's body, via the 6 o'clock incision in the fornix.

(6) Left and right rigid structures 51 are inserted, respectively, via the 2 o'clock and 10 o'clock incisions in the fornix.

(7) Tube-guide 26 is coupled to the fornix-engaging structure, via coupling elements 33. During the coupling of the tube-guide to the fornix-engaging structure, tubes are inserted into holes 60 of the tube-guide, and rigid structures 51 are inserted into holes 61 of the tube-guide. Thus by being coupled to the fornix engaging structure, the tube-guide guides the tubes and the rigid structures to their respective intra-procedural sites.

(8) Balloons 28 on the distal ends of tubes 29 are inflated such that the left and right uterine arteries are compressed, by the broad ligaments and uterine arteries being compressed against the rigid structures.

Figure 4B:
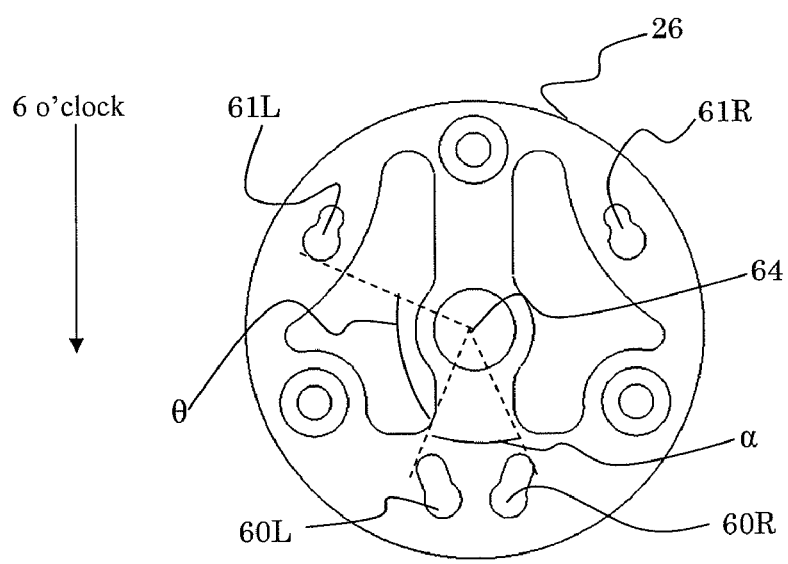

Reference is now made to FIG. 4B, which is a schematic top-view illustration of tube-guide 26, in accordance with some applications of the invention. For some applications, an angle theta, defined by hole 61L (through which rigid structure 51L is guided), longitudinal axis 64 of the tube-guide, and hole 60L (through which tube 29L is guided), is greater than 100 degrees. Similarly, the angle defined by hole 61R (through which rigid structure 51R is guided), longitudinal axis 64 of the tube-guide, and hole 60R (through which tube 29R is guided), is greater than 100 degrees. For some applications, an angle alpha defined by left hole 60L, longitudinal axis 64 of the tube-guide, and right hole 60R, is less than 10 degrees.

Figure 5:
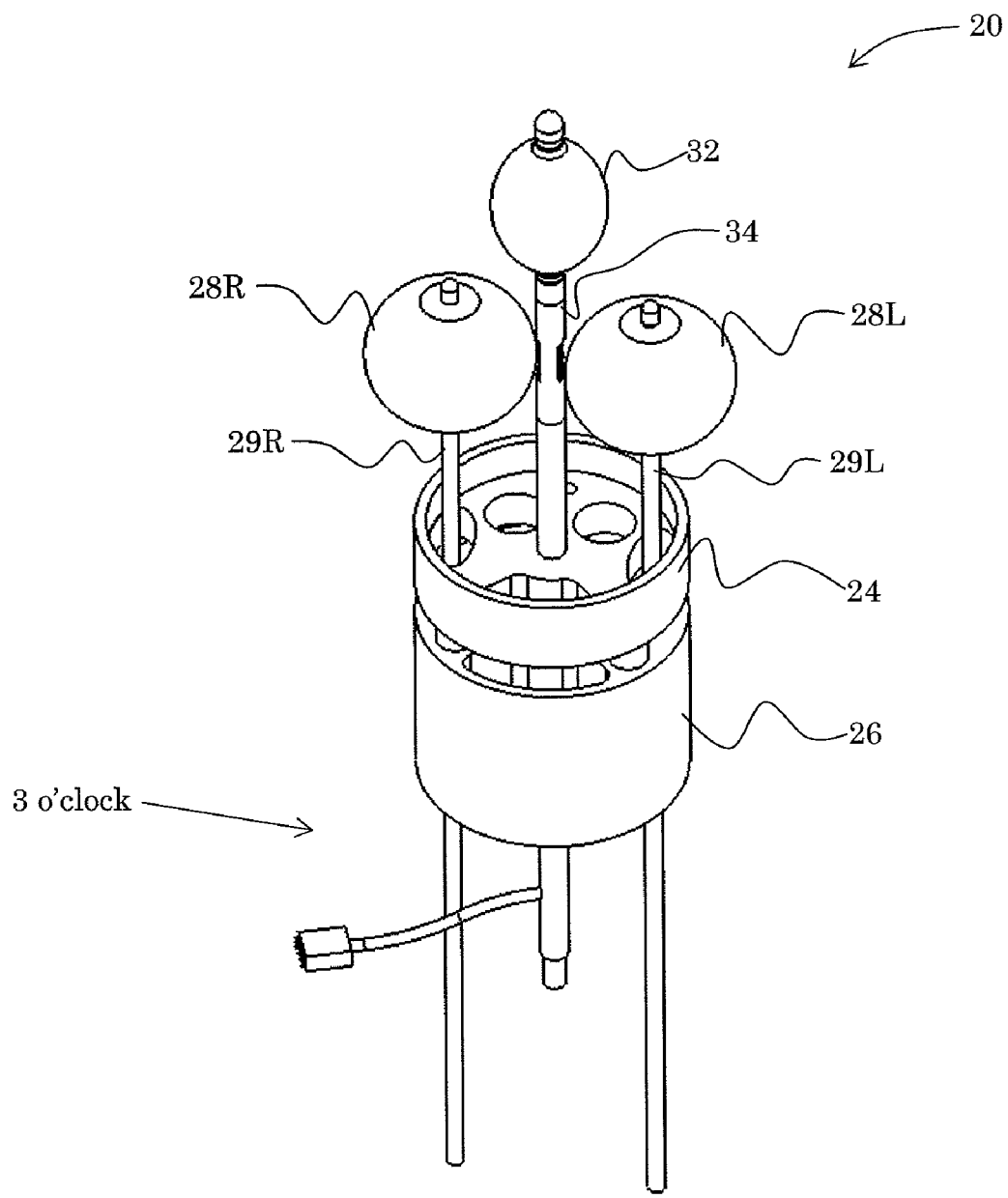
FIG. 5 is a schematic illustration of the device configured to at least partially occlude a subject's uterine arteries, in accordance with some applications of the present invention.

Reference is now made to FIG. 5, which is a schematic illustrations of device 20, in accordance with some applications of the present invention. As stated hereinabove, for some applications, left and right balloons 28L and 28R are inserted into sites on both the left and right side of the subject's cervix via incisions at approximately 3 o'clock and 9 o'clock positions with respect to the subject's uterus. Device 20, as used for such applications, is shown in FIG. 5. Fornix-engaging structure 24 and tube-guide 26 each define holes at the 3 o'clock and 9 o'clock positions. Tubes 29L and 29R are inserted through incisions in the vaginal tissue at the 3 o'clock and 9 o'clock positions by fornix-engaging structure 24 being pushed against the subject's fornix, and the tubes being inserted through the holes in the structure. For some applications, subsequent to the fornix-engaging structure 24 being pushed against the fornix, and/or subsequent to the tubes having been inserted through the holes in structure 24, tube-guide 26 is coupled to structure 24, via coupling elements 33. The tube-guide guides left and right tubes 29L and 29R to their respective positions, by being coupled to the fornix-engaging structure.

Figure 6A:
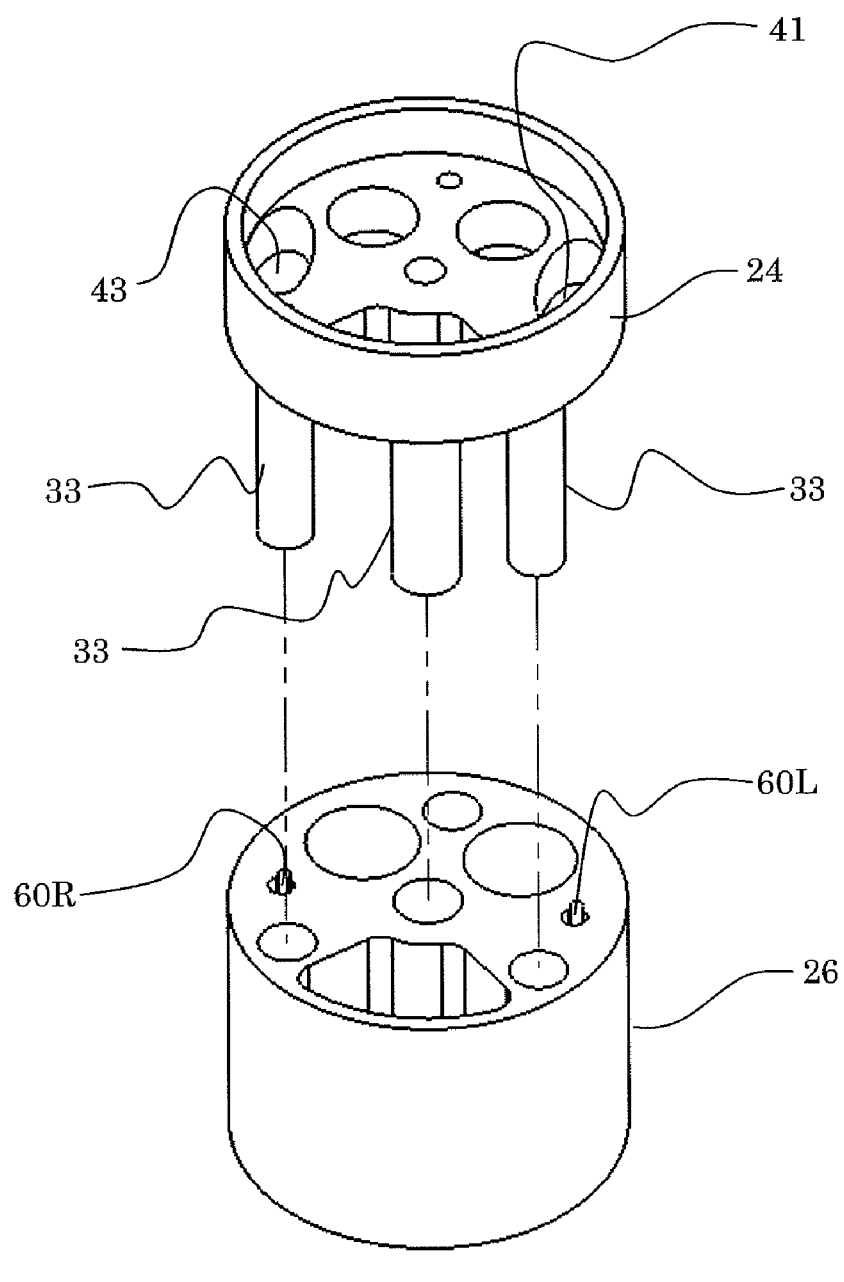
FIGS. 6A-C are schematic illustrations of a tube-guide, in accordance with some applications of the present invention.
Figure 6B:
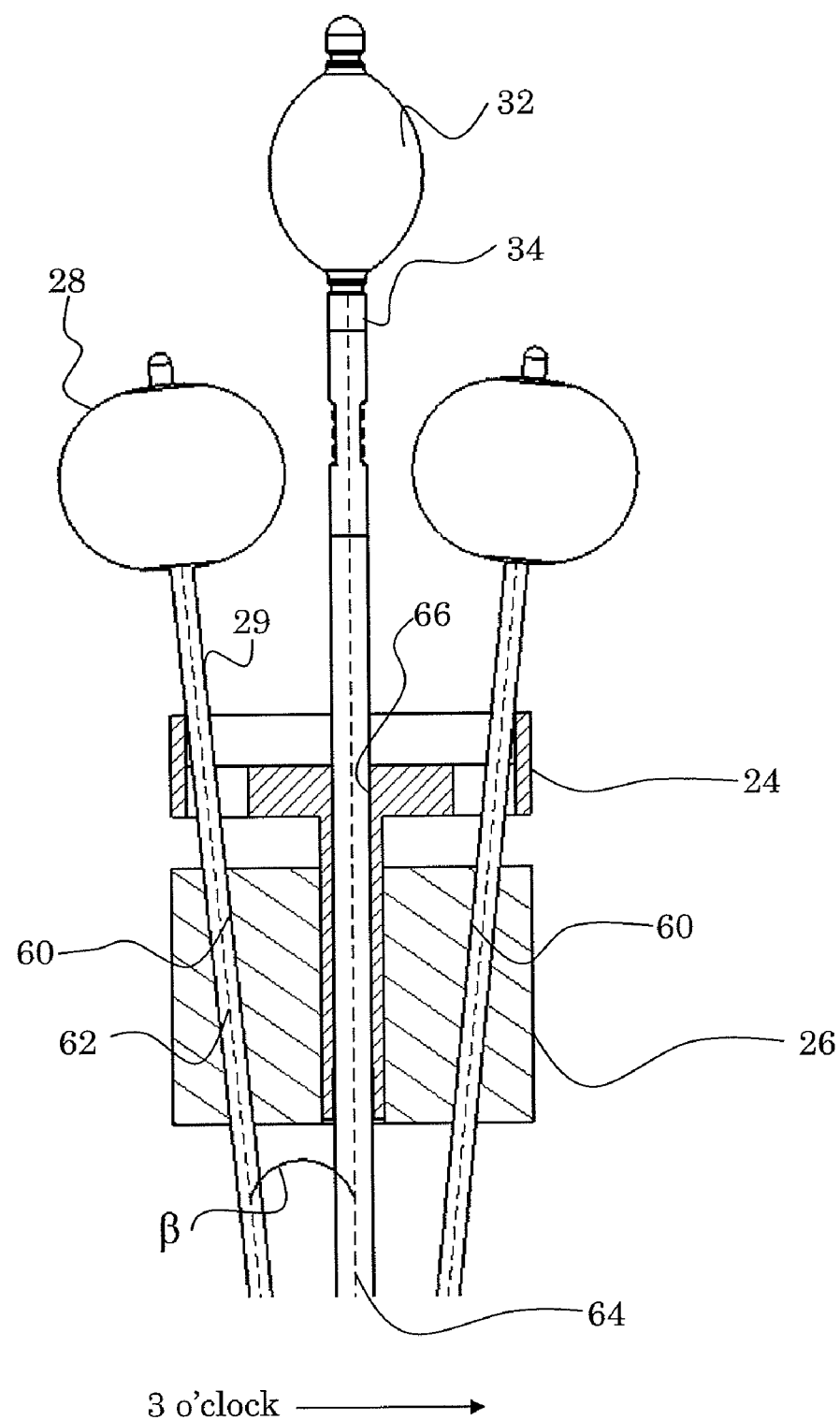
Figure 6C:
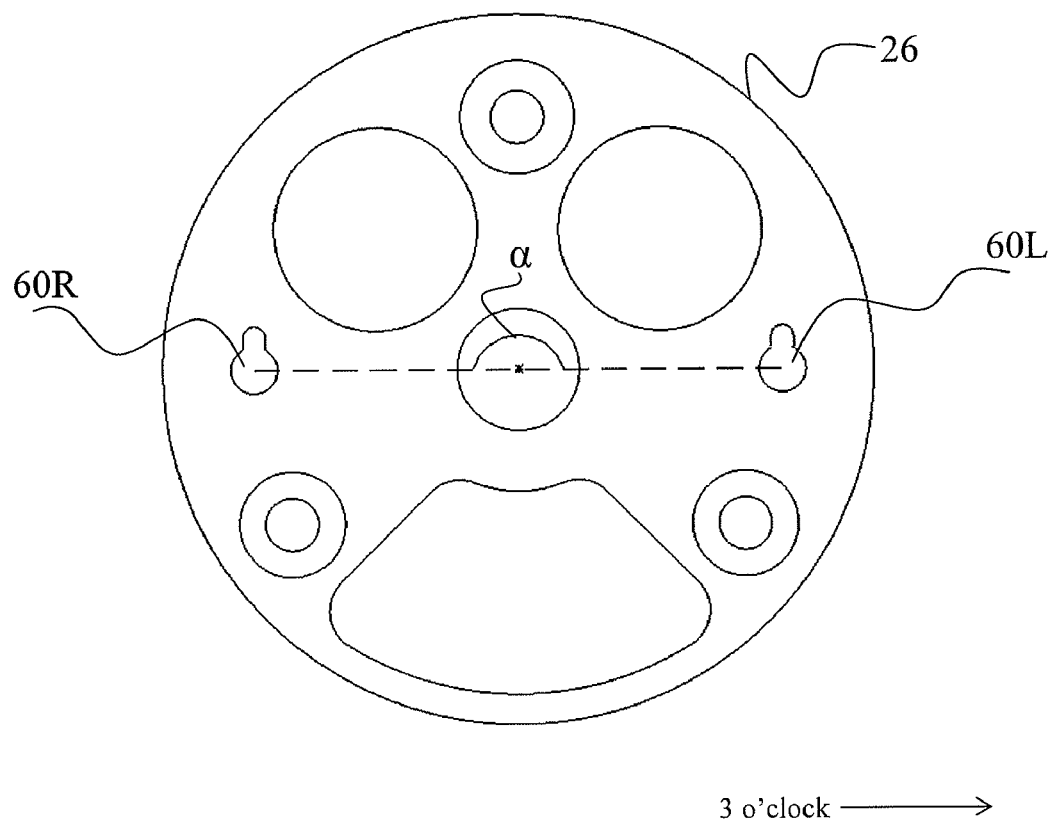

Reference is now made to FIGS. 6A-C, which are schematic illustrations of components of device 20, in accordance with some applications of the present invention. The fornix-engaging structure 24 and tube-guide 26, shown in FIGS. 6A-C, are typically used in techniques in which incisions 22 are made in the vaginal tissue at approximately 3 o'clock and 9 o'clock positions with respect to the subject's uterus (i.e., as shown in FIG. 5). However, some of the elements of device 20 described with reference to FIGS. 6A-C are also used with the fornix-engaging structure and tube-guide as described elsewhere in this application.

For some applications, device 20 is placed inside the subject's body in accordance with the following procedure:

(1) Positioning-anchoring tube 34 and positioning-anchoring balloon 32 are coupled to fornix-engaging structure 24.

(2) Before or after step (1), fornix-engaging structure 24, is inserted into the subject's vagina such that it engages the subject's fornix, and such that the distal end of positioning-anchoring tube 34 and balloon 32 are placed inside the subject's uterus, via the subject's cervix.

(3) Positioning-anchoring balloon 32 is inflated so as to position and anchor the fornix-engaging structure.

(4) Incisions are made in the fornix (a) at the 3 o'clock position, via hole a hole 41 in structure 24, and (b) at the 9 o'clock position, via a hole 43 in structure 24.

(5) Left and right tubes 29 are inserted into the extrauterine space inside the subject's body, via, respectively, the 3 o'clock and 9 o'clock incisions in the fornix.

(6) Tube-guide 26 is coupled to the fornix-engaging structure, via coupling elements 33. During the coupling of the tube-guide to the fornix-engaging structure, tubes 29 are inserted into holes 60 of the tube-guide. Thus, by being coupled to the fornix engaging structure, the tube-guide guides the tubes to their respective intra-procedural sites.

(8) Balloons 28 on the distal ends of tubes 29 are inflated such that the left and right uterine arteries are compressed, typically, by tissue being compressed against a portion of device 20, e.g., positioning-anchoring tube 34.

For some applications, as shown in FIG. 6B, longitudinal axis 62 of hole 60 is not parallel to longitudinal axis 64 of the fornix-engaging structure. For example, axis 62 may be at an angle beta of even as large as 60 degrees, although beta is typically less than 60 degrees, e.g., 10 degrees to 45 degrees from axis 64, for example, 15 degrees to 30 degrees from axis 64. For some applications, due to the orientation of hole 60, tube 29 is inserted into the subject's body at an angle to axis 64. For some applications, this ensures that the distal end of tube 29 becomes positioned in a suitable position for balloon 28 to occlude the subject's uterine artery.

For some applications, the length of tube 29 that protrudes from structure 24 into the subject's body is between 1 cm and 6 cm. For some applications, tube 29 includes a stopper (not shown) at its distal end, in order to prevent the tube from being inserted too far through the tube-guide. For example, a stopper may be used as described in PCT Publication WO 08/012802 to Gross, which is incorporated herein by reference, mutatis mutandis.

For some applications, tube-guide 26 defines a further hole 66, through which positioning-anchoring tube is inserted into the subject's uterus. For some applications, positioning-anchoring tube 34 includes a stop at its distal end in order to prevent the positioning-anchoring tube from being inserted too far through the tube-guide.

For some applications, as shown in FIG. 6C, hole 60 is not circular. (Alternatively, hole 60 is circular.) For some applications, tube 29 is shaped such that the cross-section of tube 29 has the same shape as that of hole 60. Further typically, tube 29 and hole 60 are shaped so as to prevent tube 29 from rotating with respect to tube-guide 26.

For some applications, angle alpha defined by left hole 60L in tube-guide 26, longitudinal axis 64 of the tube-guide, and right hole 60R in tube-guide 26, is between 170 and 190 degrees.

Figure 7:
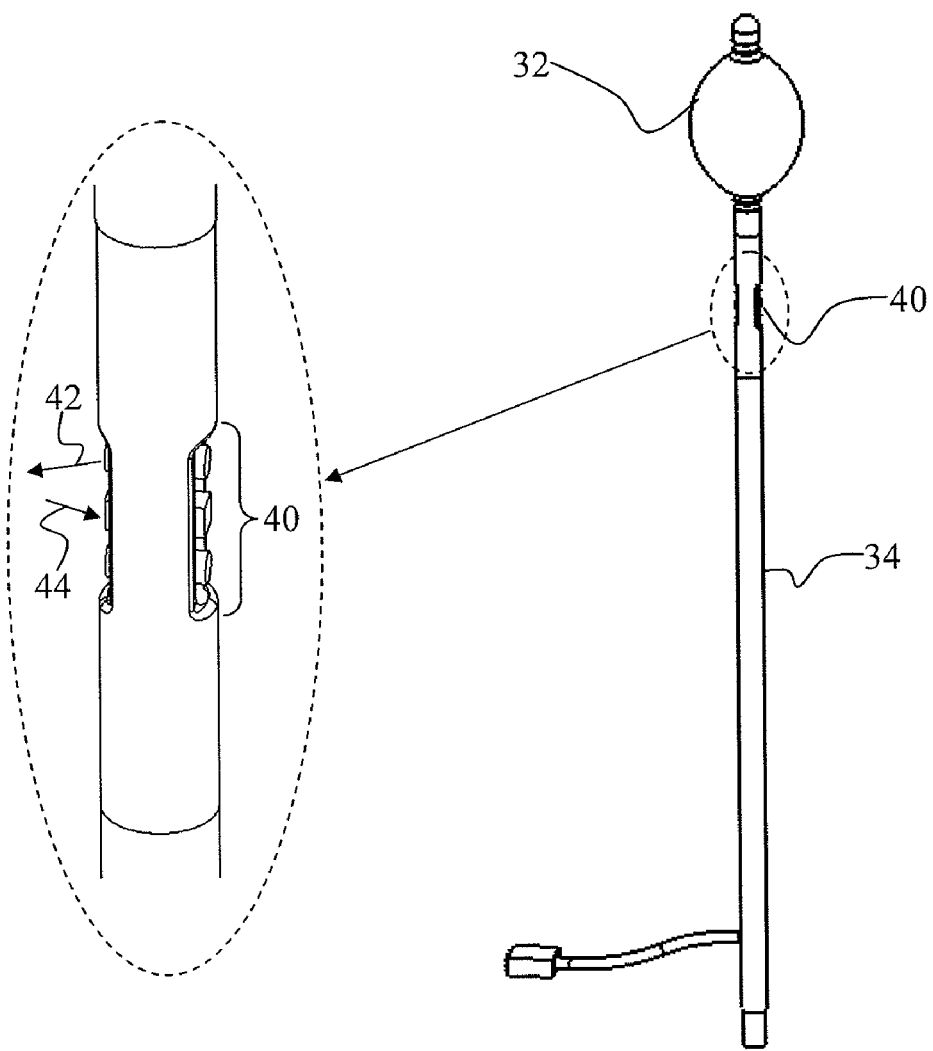
FIG. 7 is a schematic illustration of a positioning-anchoring balloon, and a positioning-anchoring tube that includes an oximetry system, in accordance with some applications of the present invention.

Reference is now made to FIG. 1, and to FIG. 7, which is an enlarged schematic illustration of positioning-anchoring tube 34 and positioning-anchoring balloon 32, in accordance with some applications of the present invention. For some applications, device 20 includes one or more sensors for monitoring blood flow, in order to evaluate the occlusion of the uterine artery. For example, a microphone 46 detects sound waves that are generated from the uterine artery at site 30 (shown in FIG. 1), and/or at balloon 55 (application not shown), and/or a pressure sensor 48 detects the pressure inside balloon 28 (shown in FIG. 1), balloon 32 (shown in FIG. 1), and/or balloons 55 (application not shown).

For some applications, the sensors are coupled to positioning-anchoring tube 34. For example, device 20 may include one or more oximeters 40, which are coupled to positioning-anchoring tube 34, as shown. The oximeters emit light (e.g., red and infrared light) toward the cervix, or toward tissue in the vicinity of the cervix, and detect the light that is reflected from the cervix, or from the tissue. For example, light is emitted in the direction of arrows 42, and light that is reflected in the direction of arrows 44 is detected. For some applications, the emitted and reflected beams of light are parallel to each other. Alternatively, the light is emitted in generally all directions, and a portion of the reflected light is detected. A pulse oximeter control unit 49 (shown in FIG. 1) is typically configured to detect capillary flow in the cervix by the oximeter detecting a level of oxyhemoglobin and/or deoxyhemoglobin in the cervix.

For some applications, a physician modulates the pressure inside balloon 28 responsively to one or more of the parameters detected by the sensors. For example, the physician may modulate the pressure using a pump 50 (shown in FIG. 1) that is in fluid communication with balloon 28. Alternatively, a control unit 52 (shown in FIG. 1) modulates the pressure of balloon 28 responsively to the detected parameters, in order to achieve occlusion of the uterine artery. For some applications, the techniques described herein for monitoring and modulating the pressure of balloon 28 are used for monitoring and modulating the pressure of positioning-anchoring balloon 32. (It is noted that, although separate control units are shown in FIG. 1 for controlling the pressure in each of the balloons, for some applications a single control unit is used to monitor and/or modulate the pressure in two or more of the balloons.) For some applications, the techniques described herein for monitoring and modulating the pressure of balloon 28 are used for monitoring and modulating the pressure of balloons 55L and 55R (application not shown).

For some applications, control unit 52 determines that blood flow through the uterine artery has stopped by detecting that there is zero blood flow in the vicinity of a sensor. For some applications, the sensors described herein detect non-zero blood flow in the vicinity of the sensor, even when the portion of the uterine artery that is downstream of the occlusion is fully occluded. This is due to blood flow through other blood vessels in the vicinity, and/or due to blood motion in the portion of the artery that is upstream of the occlusion and that continues to empty and fill, even when the artery is occluded. For some applications, control unit 52 determines that blood flow through the uterine artery has stopped by detecting that a value that (a) is associated with the parameter detected by one of the sensors, and (b) is indicative of blood flow in the vicinity, has changed and then plateaued at a value indicating non-zero blood flow through at least one other of the blood vessels and/or due to blood flow through the portion of the uterine artery that is upstream of the occlusion.

For some applications, even when the value of the parameter plateaus, the value of the parameter still includes a cyclical time-varying component. As such, in the context of the present application, the meaning of the term "plateau" should be interpreted as including a value that may include a cyclical time-varying component, but that has changed and plateaued relative to an original value.

For some applications, the control unit determines that the uterine artery is occluded by determining that light detected by oximeter 40 indicates that a level of oxyhemoglobin in the vicinity of the subject's uterine artery has decreased and then plateaued at a non-zero value. This is indicative of the fact that blood-flow through the uterine artery has stopped, but there is non-zero blood flow through other blood vessels in the vicinity of the uterine artery and/or due to blood motion through the portion of the uterine artery that is upstream of the occlusion.

Alternatively, the control unit may determine that the uterine artery is occluded in response to a pulsating component of the balloon pressure that is detected by pressure sensor 48. Typically, when balloon 28 is inflated at site 30, or balloon 55 is inflated, initially a pulsating component of the pressure signal begins to be detected, and then the strength of the pulsating component increases, as the balloon makes contact with the uterine artery, or tissue that is adjacent to the uterine artery. Subsequently, the strength of the pulsating component decreases as the uterine artery becomes occluded. For some applications, when the uterine artery becomes fully occluded, pressure sensor 48 detects a non-zero pulsating component, due to blood flow through other blood vessels in the vicinity of the uterine artery and/or due to blood motion through the portion of the uterine artery that is upstream of the occlusion.

For some applications, balloon 28, balloon 32, and/or balloon 55 is made of a non-stretchable material, such as reinforced nylon, polyurethane, and/or a similar material, in order to facilitate accurate pressure measurements of the balloon by pressure sensor 48. During use, the non-stretchable balloon is configured not to reach its maximum volume, but rather to be volume restricted by the tissue in the vicinity of the balloon. Thus, the pressure required to inflate the balloon is equal to the pressure in the volume-restricting surrounding tissue. Thus, the non-stretchable balloon facilitates monitoring the pressure of the tissue surrounding the balloon. For some applications, the occlusion of the uterine artery is monitored utilizing an electronic system similar to systems utilized in common blood pressure monitoring systems, in which a non-stretchable balloon is inflated while being volume restricted between the arm and an outer fabric sleeve. Typically, the non-stretchable balloon is inserted into the subject's body in a deflated state. Further typically, the non-stretchable balloon is folded during insertion of the balloon into the subject's body, in order to enable passage of the balloon through small incisions. It is noted that, typically, the deflated volume and longitudinal footprint of a non-stretchable balloon are larger than those of a stretchable balloon that has the same maximum volume. It is further noted that before a non-stretchable is inflated, the tissue-contacting surface of the balloon is typically not smooth. Rather, the surface typically includes unopened folds of the material.

Alternatively, balloon 28, balloon 32, and/or balloon 55 is made of a stretchable material, such as latex, silicone, and/or similar materials. Typically, during the inflation of a stretchable balloon, a first portion of the inflation pressure is used to stretch the stretchable material. A second portion of the inflation pressure is associated with overcoming the pressure exerted on the balloon by the surrounding tissue that contacts the balloon. Thus, a stretchable balloon typically does not facilitate accurate blood pressure monitoring of the arteries that are in the vicinity of the balloon (although the measurements may in any case be sufficiently accurate for identifying occlusion). Using a stretchable balloon typically facilitates insertion of the balloon via a small incision, since the deflated volume and longitudinal footprint of the deflated stretchable balloon are small compared with those of a non-stretchable balloon. A stretchable balloon typically inflates in a generally smooth and uniform manner.

For some applications, balloon 28, balloon 32, and/or balloon 55 is made from two materials. For example, a non-stretchable sheet may be welded to a stretchable sheet, so as to enable stretching of the balloon in a first direction (e.g., toward the uterine arteries), while inhibiting stretching of the balloon in a second direction (embodiment not shown). The scope of the present invention includes using for balloon 28, balloon 32, and/or balloon 55 any combination of stretchable, non-stretchable, stiff, and/or other types of materials, as would be apparent to one skilled in the art.

For some applications, one or more of balloons 28, 32, and 55 is made of a non-stretchable material, in order to facilitate accurate pressure measurements of the balloon by pressure sensor 48, and one or more of the other balloons of balloons 28, 32, and 55 is made of a stretchable material, such as latex.

For some applications, the control unit determines that the uterine artery is occluded, in response to a pulsating component of sound waves detected by microphone 46 decreasing in value and plateauing at a non-zero-value. For some applications, when the uterine artery becomes fully occluded, the microphone detects a non-zero pulsating component of the sound waves due to blood flow through other blood vessels in the vicinity of the uterine artery and/or due to blood motion through the portion of the uterine artery that is upstream of the occlusion.

Figure 8A:
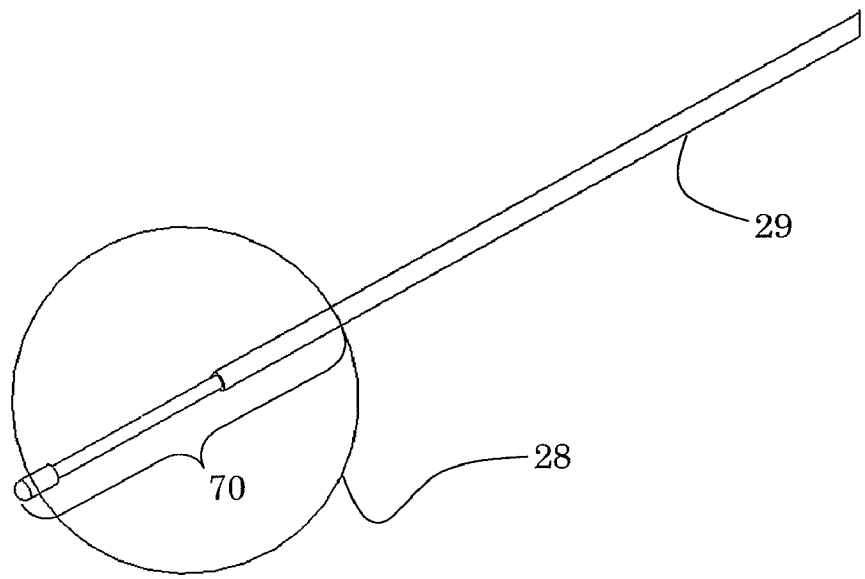
FIGS. 8A-C are schematic illustrations of a balloon for occluding the uterine artery, in accordance with respective applications of the present invention.
Figure 8B:
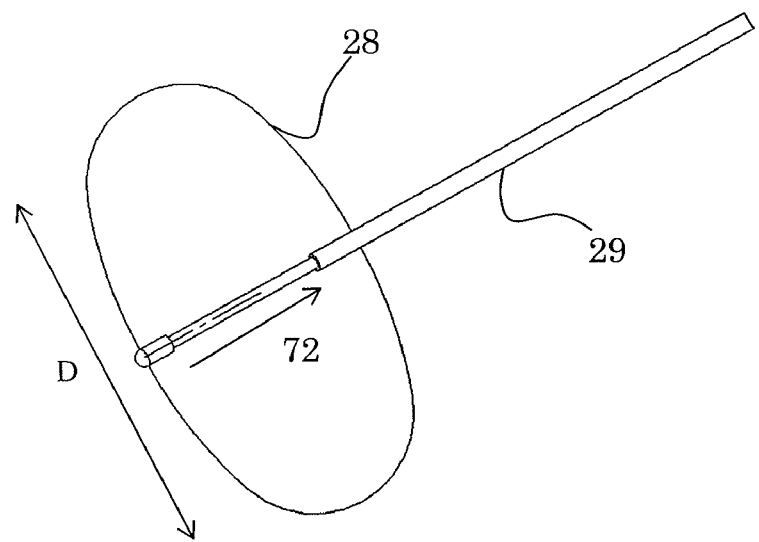
Figure 8C:
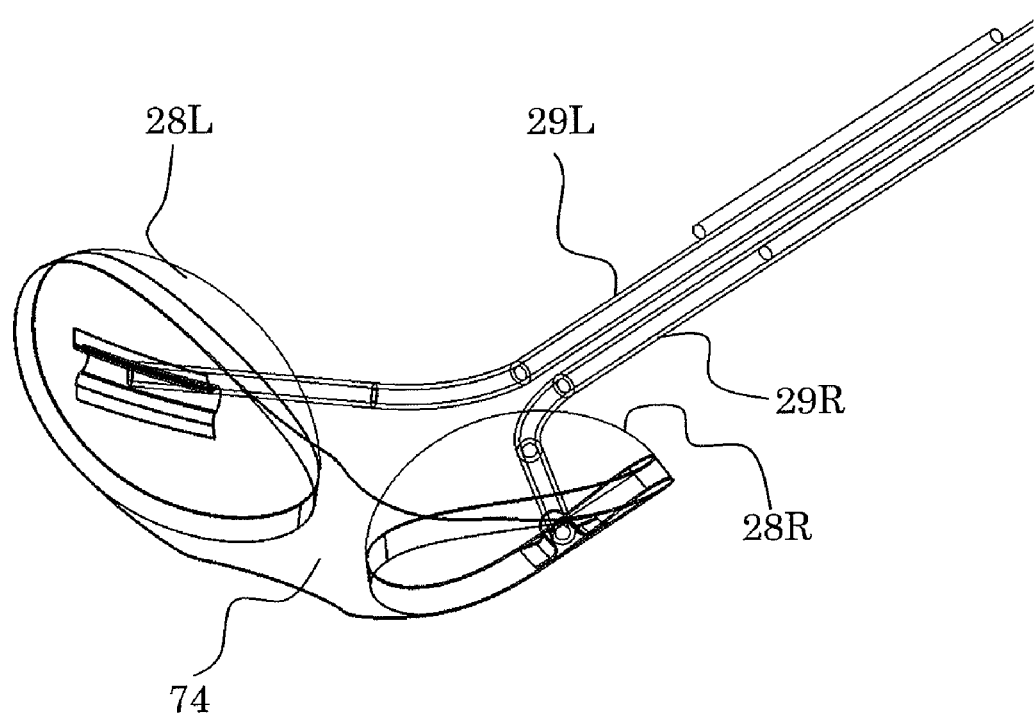

Reference is now made to FIGS. 8A-C, which are schematic illustrations of a balloon 28 for occluding the uterine artery, in accordance with an application of the present invention. For some applications, a balloon as is known in the prior art is used as uterine artery compression device 28 of device 20. In general, the scope of the present invention is not limited to using balloons as described in FIGS. 8A-C for the uterine artery compression device of device 20. It is further noted that the scope of the present invention includes using a balloon that is disposed in a non-coaxial position at the distal end of tube 29, to occlude that uterine artery.

For some applications, as shown in FIGS. 8A-B, tube includes a telescoping portion 70 at a distal end thereof. As shown in FIG. 8A, balloon 28 is inflated. Then, as shown in FIG. 8B, the telescoping portion is shortened, for example, by the distal end of the tube being retracted proximally, in the direction of arrow 72. Typically, shortening the telescoping portion causes the balloon to become more elliptical, and for the diameter D of the balloon to increase in a direction that is perpendicular to the longitudinal axis of tube 29. For some applications, increasing the diameter of the balloon in this direction is performed in this manner, in order to further compress the uterine artery.

Reference is now made to FIG. 8C, which is a schematic illustration of left and right balloons 28, in accordance with some applications of the present invention. For some applications, the left and right balloons are inserted into the subject's body via a single vaginal incision, for example, at the 6 o'clock position, as described with reference to FIG. 3A-E. For some applications, the balloons are coupled to a flexible backing material 74 that is non-stretchable, and that couples the two balloons to each other, as shown in FIG. 8C. For some applications, backing material 74 defines a maximum distance between respective centers of the left and right uterine balloons of, for example 5-25 cm, e.g., 12 cm. Alternatively, backing material 74 is stretchable, or comprises a combination of stretchable and non-stretchable materials. For some applications, backing material 74 is made of reinforced nylon, polyurethane, and/or a similar material. The backing material typically ensures that the inflation of the balloons is substantially on the other side of each the balloons to the side that is coupled to the backing material. Furthermore, the backing material typically correctly positions each of the balloons with respect to the other balloon.

Included within the scope of the present invention is a positioning-anchoring balloon that is inserted into a subject's uterus and which, by engaging the subject's uterus by being inflated, positions, and then anchors a medical tool that is in an extrauterine location within the subject's body.

Although applications are described herein relating to using a balloon as a uterine artery compression device, the scope of the present invention includes using other devices (e.g., solid or flexible devices) for occluding the uterine artery instead of or in addition to a balloon, mutatis mutandis.

Although applications are described herein relating to using a balloon on a telescoping pole for uterine artery compression, the scope of the present invention includes using a balloon on a telescoping pole, as described herein, for a different purpose, e.g., to compress a different artery, or organ.

For some applications, the apparatus and methods described herein are practiced in combination with apparatus and methods described in PCT Publication WO 08/012802 to Gross, which is incorporated herein by reference.

It is noted that although some applications of the present invention are described herein in the context of a transvaginal procedure, the scope of the present invention includes performing some or all of the procedure laparoscopically.

The terms "guide structure," "tube-guide," and "rod guide" are used in the present application. A "tube guide" is a type of "rod guide," and a "rod guide" is a type of "guide structure." The scope of the present invention includes using any rod guide (e.g., a solid rod guide) in place of a tube guide, for applications in which the use of a tube guide is described, mutatis mutandis. The scope of the present invention further includes using a different guide structure in place of a tube guide or a rod guide, for applications in which the use of a tube guide or a rod guide is described, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, for use with a subject's body, vagina, vaginal formix, uterus, and uterine artery, the method comprising:
    engaging the vaginal formix with a formix-engaging structure, by inserting the structure into the vagina;
    inserting a rod into the subject's body;
    guiding the rod such that a distal end of the rod passes through vaginal tissue at a first vaginal site until the distal end of the rod is at a first extrauterine site outside of the uterine artery, but in a vicinity of a portion of the uterine artery that supplies a uterine fibroid;
    maintaining the distal end of the rod at the extrauterina site, by supporting the rod with the formix-engaging structure; and
    while maintaining the distal end of the rod at the extrauterina site, compressing the uterine artery using a uterine artery compression device disposed on the distal end of the rod to occlude blood flow to a uterine fibroid.

2. The method according to claim 1, wherein the uterine artery compression device includes a balloon, and wherein compressing the uterine artery using the uterine artery compression device comprises inflating the balloon.

3. The method according to claim 1, wherein inserting the rod into the subject's body comprises inserting a rigid rod into the subject's body, and wherein compressing the uterine artery using the uterine artery compression device disposed on the distal end of the rod, comprises maintaining the position of the distal end of the rod at the extrauterina site, using the rigidity of the rod.

4. The method according to claim 1,
    further comprising inserting a rigid structure into the subject's body, and guiding the rigid structure such that a distal end of the rigid structure passes through vaginal tissue at a second vaginal site, until the distal end of the rigid structure is at a second extrauterine site outside of the uterine artery,
    wherein compressing the uterine artery using the uterine artery compression device comprises compressing the uterine artery by squeezing tissue of the subject against the rigid structure, using the uterine artery compression device.

5. The method according to claim 4,
    wherein guiding the rod such that the distal end of the rod is at the first extrauterine site comprises guiding the rod such that the distal end of the rod is at an extrauterine site that is posterior to a broad ligament of the subject, and
    wherein guiding the rigid structure such that the distal end of the rigid structure is at the second extrauterine site comprises guiding the distal end of the rigid structure to a second extrauterine site that is anterior to the broad ligament of the subject.

6. The method according to claim 1, wherein inserting the rod comprises inserting a solid rod.

7. The method according to claim 1, wherein inserting the rod comprises inserting a hollow rod.

8. The method according to claim 1, further comprising detecting a change in blood flow through the uterine artery.

9. The method according to claim 1, further comprising positioning and anchoring the uterine artery compression device while the uterine artery compression device is at the site, by placing a positioning-anchoring balloon inside the uterus and inflating the positioning-anchoring balloon while the positioning-anchoring balloon is inside the uterus.

10. The method according to claim 1, wherein compressing the uterine artery comprises squeezing tissue of the subject against a medical tool in the subject's body, using the uterine artery compression device.

11. The method according to claim 1, wherein:
- the rod includes left and right rods, and the uterine artery compression device includes left and right uterine artery compression devices disposed, respectively, on distal ends of the left and right rods,
- guiding the rod comprises guiding the left and right rods, via left and right first vaginal sites, such that distal ends of the rods are at left and right first extrauterine sites outside of but in a vicinity of left and right uterine arteries of the subject, respectively, and
- compressing the uterine artery comprises compressing the left and right uterine arteries, using, respectively, the left and right uterine artery compression devices.

12. The method according to claim 11, wherein guiding the left and right rods comprises guiding the rods to the left and right first extrauterine sites via vaginal tissue at approximately a six o'clock position with respect to the subject's uterus.

13. The method according to claim 11,
- wherein guiding the left rod comprises guiding the left rod to the left first extrauterine site via vaginal tissue at approximately a three o'clock position with respect to the subject's uterus, and
- wherein guiding the right rod comprises guiding the right rod to the right first extrauterine site via vaginal tissue at approximately a nine o'clock position with respect to the subject's uterus.

* * * * *